US006867349B2

(12) United States Patent
Ekker et al.

(10) Patent No.: US 6,867,349 B2
(45) Date of Patent: Mar. 15, 2005

(54) INHIBITION OF GENE EXPRESSION USING POLYNUCLEOTIDE ANALOGUES

(75) Inventors: Stephen C. Ekker, St. Paul, MN (US); Aidas Nasevicius, St. Paul, MN (US); Hyon Kim, Minneapolis, MN (US); Saulius Sumanas, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/918,242

(22) Filed: Jul. 30, 2001

(65) Prior Publication Data

US 2002/0078471 A1 Jun. 20, 2002

Related U.S. Application Data

(60) Provisional application No. 60/221,722, filed on Jul. 31, 2000, provisional application No. 60/252,864, filed on Nov. 22, 2000, and provisional application No. 60/284,974, filed on Apr. 19, 2001.

(51) Int. Cl.[7] .............................................. C12N 15/00
(52) U.S. Cl. ............................ 800/21; 800/20; 800/25; 514/44
(58) Field of Search ............................. 800/20, 21, 25, 800/8, 4; 514/44; 536/23.1; 531/24.5

(56) References Cited

U.S. PATENT DOCUMENTS

| | | | |
|---|---|---|---|
| 5,142,047 A | | 8/1992 | Summerton et al. |
| 5,185,444 A | | 2/1993 | Summerton et al. |
| 5,563,255 A | * | 10/1996 | Monia et al. ............ 536/24.31 |
| 5,726,059 A | | 3/1998 | Wickens et al. |
| 5,734,033 A | * | 3/1998 | Reed ........................ 536/23.1 |

FOREIGN PATENT DOCUMENTS

WO   WO 95/31459   11/1995

OTHER PUBLICATIONS

Roth, L. et al. Beta–Thymosin is required for axonal tract formation in developing zebrafish brain. Development, Apr. 1999; vol. 126, No. 7, pp. 1365–1374.*
Heasman, J. Morpholino oligos: making sense of antisense. Dvelopmental Biology, 2002; vol. 243, pp. 209–214.*
Ekker et al., "Morphant Technology in Model Developmental Systems," *Genesis*, 2001, 30:89–93.
Morcos, "Achieving Efficient Delivery of Morpholino Oligos in Cultured Cells," *Genesis*, 2001, 30:94–102.
Satou et al., "Action of Morpholinos in Ciona Embryos," *Genesis*, 2001, 30:103–106.
Audic et al., "Cyclin E Morpholino Delays Embryogenesis in Xenopus," *Genesis*, 2001, 30:107–109.
Nutt et al., "Comparison of Morpholino Based Translational Inhibition During the Development of *Xenopus laevis* and *Xenopus tropicalis*," *Genesis*, 2001, 30:110–113.

Sumanas et al., "Zebrafish frizzled–2 Morphant Displays Defects in Body Axis Elongation," *Genesis*, 2001, 30:114–118.
Sumanas et al., "Xenopus frizzled–7 Morphant Displays Defects in Dorsoventral Patterning and Convergent Extention Movements during Gastrulation," *Genesis*, 2001, 30:119–122.
Klee et al., "Target Selection for *Danio rerio* Functional Genomics," *Genesis*, 2001, 30:123–125.
Karlen et al., "A Morpholino Phenocopy of the cyclops Mutation," *Genesis*, 2001, 30:126–128.
Scholpp et al., "Morpholino–Induced Knockdown of Zebrafish Engrailed Genes eng2 and eng3 Reveals Redundant and Unique Functions in Midbrain–Hindbrain Boundary Development," *Genesis*, 2001, 30:129–133.
Huang et al., "Pdx–1 Knockdown Reduces Insulin Promoter Activity in Zebrafish," *Genesis*, 2001, 30:134–136.
Yee et al., "Zebrafish pdx1 Morphant Displays Defects in Pancreas Development and Digestive Organ Chirality, and Potentially Identifies a Multipotent Pancreas Progenitor Cell," *Genesis*, 2001, 30:137–140.
Wallace et al., "Zebrafish hhex Regulates Liver Development and Digestive Organ Chirality," *Genesis*, 2001, 30:141–143.
Schweickert et al., "Pitx1 and Pitx2c Are Required for Ectopic Cement Gland Formation in *Xenopus laevis*," *Genesis*, 2001, 30:144–148.
Cui et al., "Inhibition of skiA and skiB Gene Expression Ventralizes Zebrafish Embryos," *Genesis*, 2001, 30:149–153.
Draper et al., "Inhibition of Zebrafish fgf8 Pre–mRNA Splicing With Morpholino Oligos: A Quantifiable Method for Gene Knockdown," *Genesis*, 2001, 154–156.
Araki et al., "Morpholino–Induced Knockdown of fgf8 Efficiently Phenocopies the Acerebellar (Ace) Phenotype," *Genesis*, 2001, 30:157–159.
Imai et al., "Morpholino Phenocopies of the bmp2b/swirl and bmp7/snailhouse Mutations," *Genesis*, 2001, 30:160–163.
Etheridge et al., "Floor Plate Develops Upon Depletion of Tiggy–winkle and Sonic Hedgehog," *Genesis*, 2001, 30:164–169.
Bingham et al., "Sonic Hedgehog and Tiggy–Winkle Hedgehog Cooperatively Induce Zebrafish Branchiomotor Neurons," *Genesis*, 2001, 30:170–174.

(List continued on next page.)

*Primary Examiner*—Dave T. Nguyen
*Assistant Examiner*—Jon Eric Angell
(74) *Attorney, Agent, or Firm*—Fish & Richardson P.C., P.A.

(57) ABSTRACT

The invention provides sequence specific polynucleotide analogues and methods for determining the function of a nucleic acid of known sequence.

8 Claims, 10 Drawing Sheets

OTHER PUBLICATIONS

Feldman et al., "Morpholino Phenocopies of sqt, oep, and ntl Mutations," *Genesis*, 2001, 30:175–177.

Agathon et al., "Morpholino Knock–Down of Antivin1 and Antivin2 Upregulates Nodal Signaling," *Genesis*, 2001, 30:178–182.

Braat et al., "A Zebrafish Vasa Morphant Abolishes Vasa Protein but Does Not Affect the Establishment of Germline," *Genesis*, 2001, 30:183–185.

Miller et al., "Morpholino Phenocopies of endothelin 1 (sucker) and Other Anterior Arch Class Mutations," *Genesis*, 2001, 30:186–187.

Dutton et al., "A Morpholino Phenocopy of the colourless Mutant," *Genesis*, 2001, 30:188–189.

Lele et al., "Morpholino Phenocopies of the swirl, snailhouse, somitabun, minifin, silberblick, and pipetail Mutations," *Genesis*, 2001, 30:190–194.

Wang et al., "Suppression of Heat Shock Transcription Factor HSF1 in Zebrafish Causes Heat–Induced Apoptosis," *Genesis*, 2001, 30:195–197.

Coonrod et al., "A Morpholino Phenocopy of the Mouse mos Mutation," *Genesis*, 2001, 30:198–200.

Amsterdam et al., "A large–scale insertional mutagenesis screen in zebrafish," *Genes Dev.*, 1999, 13:2713–2724.

Arora and Nusslein–Volhard, "Altered mitotic domains reveal fate map changes in Drosophila embryos mutant for zygotic dorsoventral patterning genes," *Development*, 1992, 114:1003–1024.

Arora et al., "c–Myc Antisense Limits Rat Liver Regeneration and Indicates Role for c–Myc in Regulating Cytochrome P–450 3A Activity," *J. Phamacol. Exp. Ther.*, 2000, 292:921–928.

Ashe and Levine, "Local inhibition and long–range enhancement of Dpp signal transduction by Sog," *Nature*, 1999, 398:427–431.

Ashe et al., "Dpp signaling thresholds in the dorsal ectoderm of the Drosophila embryo," *Development*, 2000, 127:3305–3312.

Balinsky et al., *An Introduction to Embryology*, Fifth Edition, 1981, Saunders College Publishing, Philadelphia, pp. 135–152.

Barabino et al., "Inactivation of the zebrafish homologue of Chx10 by antisense oligonucleotides causes eye malformations similar to the ocular retardation phenotype," *Mech. Dev.*, 1997, 63:133–143.

Belloni et al., "Identification of Sonic hedgehog as a candidate gene responsible for holoprosencephaly," *Nature Genetics*, 1996, 14:353–356.

Blake et al., "Inhibition of Rabbit Globin mRNA Translation by Sequence–Specific Oligodeoxyribonucleotides," *Biochemistry*, 1985, 24:6132–6138.

Blake et al., "Hybridization Arrest of Globin Synthesis in Rabbit Reticulocyte Lysates and Cells by Oligodeoxyribonucleoside Methylphosphonates," *Biochemistry*, 1985, 24:6139–6145.

Braasch and Corey, "Locked nucleic acid (LNA): fine–tuning the recognition of DNA and RNA," *Chem. Biol.*, 2001, 8:1–7.

Brown et al., "Insights into early vasculogenesis revealed by expression of the ETS–domain transcription factor Fli–1 in wild–type and mutant zebrafish embryos," *Mech. Dev.*, 2000, 90:237–252.

Carmeliet et al., "Abnormal blood vessel development and lethality in embryos lacking a single VEGF allele," *Nature*, 1996, 380:435–439.

Carmeliet and Collen, "Molecular analysis of blood vessel formation and disease," *Am. J. Physiol.*, 1997, 273 (5, Part 2):H2091–H2104.

Chang et al., "Twisted gastrulation can function as a BMP antagonist," *Nature*, 2001, 410:483–487.

Chen et al., "Mutations affecting the cardiovascular system and other internal organs in zebrafish," *Development*, 1996, 123:293–302.

Cho et al., "Molecular Nature of Spemann's Organizer: the Role of the Xenopus Homeobox Gene goosecoid," *Cell*, 1991, 67:1111–1120.

Concordet et al., "Spatial regulation of a zebrafish patched homologue reflects the roles of sonic hedgehog and protein kinase A in neural tube and somite patterning," *Development*, 1996, 122:2835–2846.

Cook, "Antisense Medicinal Chemistry," *The Medicinal Chemistry of Oligonucleotides*, 1998, Chapter 2, Springer, New York, pp. 51–101.

Darnell et al., *Molecular Cell Biology*, $2^{nd}$ Edition, 1990, Scientific American Books, W.H. Freeman and Company, New York, pp. 68–74.

Detrich III et al. (eds.), *Methods in Cell Biology*, vol. 59, 1999, Academic Press, San Diego, California, pp. 3–10.

Detrich III et al., "Intraembryonic hematopoietic cell migration during vertebrate development," *Proc. Natl. Acad. Sci. USA*, 1995, 92:10713–10717.

Dick et al., "Essential role of Bmp7 (snailhouse) and its prodomain in dorsoventral patterning of the zebrafish embryo," *Development*, 2000, 127:343–354.

Driever et al., "A genetic screen for mutations affecting embryogenesis in zebrafish," *Development*, 1996, 123:37–46.

Driver et al., "Oligonucleotide–based inhibition of embryonic gene expression," *Nat. Biotechnol.*, 1999, 17:1184–1187.

Ekker et al., "Patterning activities of vertebrate hedgehog proteins in the developing eye and brain," *Curr. Biol.*, 1995, 5(8):944–955.

Ekker and Larson, "Morphant Technology in Model Developmental Systems," *Genesis*, 2001, 30:89–93.

Fekany et al., "The zebrafish bozozok locus encodes Dharma, a homeodomain protein essential for induction of gastrula organizer and dorsoanterior embryonic structures," *Development*, 1999, 126:1427–1438.

Ferguson et al, "decapentaplegic Acts As a Morphogen to Organize Dorsal–Ventral Pattern in the Drosophila Embryo," *Cell*, 1992, 71:451–461.

Ferguson and Anderson, "Localized enhancement and repression of the activity of the TGF–$\beta$ family member, decapentaplegic, is necessary for dorsal–ventral pattern formation in the Drosophila embryo," *Development*, 1992, 114:583–597.

Ferrara et al., "Heterozygous embryonic lethality induced by targeted inactivation of the VEGF gene," *Nature*, 1996, 380:439–442.

Ferrara, "Molecular and biological properties of vascular endothelial growth factor," *J. Mol. Med.*, 1999, 77:527–543.

Fisher et al., "Loss of cerebrum function ventralizes the zebrafish embryo," *Development*, 1997, 124:1301–1311.

Fouquet et al., "Vessel Patterning in the Embryo of the Zebrafish: Guidance by Notochord," *Dev. Biol.,* 1997, 183:37–48.

Froehler et al., "Phosphoramidate analogues of DNA: synthesis and thermal stability of heteroduplexes," *Nucl. Acids Res.,* 1988, 16(11):4831–4839.

Gates et al., "A Genetic Linkage Map for Zebrafish: Comparative Analysis and Localization of Genes and Expressed Sequences," *Genome Res.,* 9:334–347.

Gerber et al., "VEGF is required for growth and survival in neonatal mice," *Development,* 1999, 126:1149–1159.

Gritsman et al., "The EGF–CFC Protein One–Eyed Pinhead Is Essential for Nodal Signaling," *Cell,* 1999, 97:121–132.

Haerry et al., "Synergistic signaling by two BMP ligands through the SAX and TKV receptors controls wing growth and patterning in Drosophila," *Development,* 1998, 125:3977–3987.

Haffter et al., "The identification of genes with unique and essential functions in the development of the zebrafish, *Danio rerio,*" *Development,* 1996, 123:1–36.

Haigh et al., "Conditional inactivation of VEGF-A in areas of collagen2a1 expression results in embryonic lethality in the heterozygous state," *Development,* 2000, 127:1445–1453.

Halpern et al., "Genetic Interactions in Zebrafish Midline Development," *Dev. Biol.,* 1997, 187:154–170.

Hammerschmidt et al., "dino and mercedes, two genes regulating dorsal development in the zebrafish embryo," *Development,* 1996, 123:95–102.

Harland and Gerhart, "Formation and Function of Speman's Organizer," *Annu. Rev. Cell Dev. Biol.,* 1997, 13:611–667.

Heasman et al., "β–Catenin Signaling Activity Dissected in the Early Xenopus Embryo: A Novel Antisense Approach," *Dev. Biol.,* 2000, 222:124–134.

Holley et al., "The Xenopus Dorsalizing Factor noggin Ventralizes Drosophila Embryos by Preventing DPP from Activating Its Receptor," *Cell,* 1996, 86:607–617.

Holley and Ferguson, "Fish are like flies are like frogs: conservation of dorsal–ventral patterning mechanisms," *BioEssays,* 1997, 19(4):281–284.

Hukriede et al., "Radiation hybrid mapping of the zebrafish genome," *Proc. Natl. Acad. Sci. USA,* 1999, 96:9745–9750.

Hunter, "Gene silencing: Shrinking the black box of RNAi," *Curr. Biol.,* 2000, 10:R137–R140.

Hyatt and Ekker, "Vectors and Techniques for Ectopic Gene Expression in Zebrafish," *Methods Cell Biol.,* 1999, 59:117–126.

Ivics et al., "Molecular Reconstruction of Sleeping Beauty, a Tc1–like Transposon from Fish, and Its Transposition in Human Cells," *Cell,* 1997, 91:501–510.

Jayaraman et al., "Selective inhibition of *Escherichia coli* protein synthesis and growth by nonionic oligonucleotides complementary to the 3' end of 16S rRNA," *Proc. Natl. Acad. Sci. USA,* 1981, 78:1537–1541.

Jowett, "Analysis of Protein and Gene Expression," *Methods Cell Biol.,* 1999, 59:63–85.

Kappas et al., "The Porphyrias," *The Metabolic and Molecular Bases of Inherited Disease, 7th Edition,* 1995, McGraw–Hill, Inc., New York, pp. 2103–2159.

Kennerdell and Carthew, "Use of dsRNA–Mediated Genetic Interference to Demonstrate that frizzled and frizzled 2 Act in the Wingless Pathway," *Cell,* 1998, 95:1017–1026.

Kishimoto et al., "The molecular nature of zebrafish swirl: BMP2 function is essential during early dorsoventral patterning," *Development,* 1997, 124:4457–4466.

Koos and Ho, "The nieuwkoid/dharma Homeobox Gene Is Essential for bmp2b Repression in the Zebrafish Pregastrula," *Dev. Biol.,* 1999, 215:190–207.

Krauss et al., "Expression of the zebrafish paired box genes pax[zf–b] during early neurogenesis," *Development,* 1991, 113:1193–1206.

Krauss et al., "A Functionally Conserved Homolog of the Drosophila Segment Polarity Gene hh Is Expressed in Tissues with Polarizing Activity in Zebrafish Embryos," *Cell,* 1993, 75:1431–1444.

Li et al., "Expression of two zebrafish orthodenticle–related genes in the embryonic brain," *Mech. Dev.,* 1994, 48:229–244.

Li et al., "Double–Stranded RNA Injection Produces Null Phenotypes in Zebrafish," *Dev. Biol.,* 2000, 217:394–405.

Liang et al., "Cloning and characterization of vascular endothelial growth factor (VEGF) from zebrafish, *Danio rerio,*" *Biochim. Biophys. Acta,* 1998, 1397:14–20.

Lister et al., "nacre encodes a zebrafish microphthalmia–related protein that regulates neural–crest–derived pigment cell fate," *Development,* 1999, 126:3757–3767.

Marques et al., "Production of a DPP Activity Gradient in the Early Drosophila Embryo through the Opposing Actions of the SOG and TLD Proteins," *Cell,* 1997, 91:417–426.

Mason et al., "Dorsal midline fate in Drosophila embryos requires twisted gastrulation, a gene encoding a secreted protein related to human connective tissue growth factor," *Genes Dev.,* 1994, 8:1489–1501.

Miller et al., "Nonionic Nucleic Acid Analogues. Synthesis and Characterization of Dideoxyribonucleoside Methylphosphonates," *Biochemistry,* 1979, 18(23):5134–5143.

Miller et al., "Oligothymidylate Analogues Having Stereoregular, Alternating Methylphosphonate/Phosphodiester Backbones," *J. Biol. Chem.,* 1980, 255(20):9659–9665.

Miller et al., "Control of ribonucleic acid function by oligonucleoside methylphosphonates," *Biochimie,* 1985, 67:769–776.

Miller–Betoglio et al., "Differential Regulation of chordin Expression Domains in Mutant Zebrafish," *Dev. Biol.,* 1997, 192:537–550.

Miller–Betoglio et al., "Maternal and Zygotic Activity of the Zebrafish ogon Locus Antagonizes BMP Signaling," *Dev. Biol.,* 1999, 214:72–86.

Muenke and Beachy, "Genetics of ventral forebrain development and holoprosencephaly," *Curr. Opin. Gen. Dev.,* 2000, 10:262–269.

Mullins et al., "Genes establishing dorsoventral pattern formation in the zebrafish embryo: the ventral specifying genes," *Development,* 1995, 123:81–93.

Murakami et al., "Characterization of Sequence–Specific Oligodeoxyribonucleoside Methylphosphonates and Their Interactions with Rabbit Globin mRNA," *Biochemistry,* 1985, 24:4041–4046.

Nasevicius and Ekker, "Effective targeted gene 'knockdown' in zebrafish," *Nature Genetics,* 2000, 26:216–220.

Nasevicius and Ekker, "The zebrafish as a novel system for functional genomics and therapeutic development applications," *Curr. Opin. Mol. Ther.,* 2001, 3(3):224–228.

Oates et al., "Zebrafish stat3 Is Expressed in Restricted Tissues During Embryogenesis and stat1 Rescues Cytokine Signaling in a STAT1–Deficient Human Cell Line," *Dev. Dyn.*, 1999, 215:352–370.

Oates et al., "Too Much Interference: Injection of Double–Stranded RNA Has Nonspecific Effects in the Zebrafish Embryo," *Dev. Biol.*, 2000, 224:20–28.

Oelgeschlager et al., "The evolutionarily conserved BMP–binding protein Twisted gastrulation promotes BMP signalling," *Nature*, 2000, 405:757–763.

Parichy et al., "Zebrafish sparse corresponds to an orthologue of c–kit and is required for the morphogenesis of subpopulation of melanocytes, but is not essential for hematopoiesis of primordial germ cell development," *Development*, 1999, 126:3425–3436.

Piccolo et al., "Dorsoventral Patterning in Xenopus: Inhibition of Ventral Signals by Direct Binding of Chordin to BMP–4," *Cell*, 1996, 86:589–598.

Pitha et al., "Poly(I–Vinyluracil): The Preparation and Interactions with Adenosine Derivatives," *Biochim. Biophys. Acta.* 1970, 204:39–48.

Pitha and Pitha, "Preparation and Properties of Poly–9–vinyladenine," *Biopolymers*, 1970, 9:965–977.

Postlethwait et al., "The Zebrafish Genome," *Methods Cell Biol.*, 1999, 60:149–163.

Qin et al., "In Vivo Evaluation of a Morpholino Antisense Oligomer Directed Against Tumor Necrosis Factor–α," *Antisense Nucleic Acid Drug Dev.*, 2000, 10:11–16.

Ransom et al., "Characterization of zebrafish mutants with defects in embryonic hematopoiesis," *Development*, 1996, 123:311–319.

Ray et al., "The control of cell fate along the dorsal–ventral axis of the Drosophila embryo," *Development*, 1991, 113:35–54.

Raz et al., "Transposition of the nematode *Caenorhabditis elegans* Tc3 element in the zebrafish *Danio rerio*," *Curr. Biol.*, 1997, 8:82–88.

Roessler et al., "Mutations in the human Sonic Hedgehog gene cause holoprosencephaly," *Nature Genetics*, 1996, 14:357–360.

Ross et al., "Twisted gastrulation is a conserved extracellular BMP antagonist," *Nature*, 2001, 410:479–483.

Sasai et al., "Xenopus chordin: A Novel Dorsalizing Factor Activated by Organizer–Specific Homeobox Genes," *Cell*, 1994, 79:779–790.

Schauerte et al., "Sonic hedgehog is not required for the induction of medial floor plate cells in the zebrafish," *Development*, 1998, 125:2983–2993.

Schier et al., "The one–eyed pinhead gene functions in mesoderm and endoderm formation in zebrafish and interacts with no tail," *Development*, 1997, 124:327–342.

Schulte–Merker et al., "no tail (ntl) is the zebrafish homologue of the mouse T (Brachyury) gene," *Development*, 1994, 120:1009–1015.

Schulte–Merker et al., "The zebrafish organizer requires chordino," *Nature*, 1997, 387:862–863.

Scott et al., "Homologues of Twisted gastrulation are extracellular cofactors in antagonism of BMP signalling," *Nature*, 2001, 410:475–478.

Segal and Gelbart, "Shortvein, a New Component of the Decapentaplegic Gene Complex in *Drosophila Melanogaster*," *Genetics*, 1985, 109:119–143.

Stainier et al., "Mutations affecting the formation and function of the cardiovascular system in the zebrabish embryo," *Development*, 1996, 123:285–292.

Strahle et al., "Axial, a zebrafish gene expressed along the developing body axis; shows altered expression in Cyclops mutant embryos," *Genes Dev.*, 1993, 7:1436–1446.

Summerton, "Morpholino antisense oligomers: the case for an RNase H–independent structural type," *Biochim. Biophys. Acta*, 1999, 1489:141–158.

Summerton and Weller, "Morpholino Antisense Oligomers: Design, Preparation, and Properties," *Antisense Nucl. Acid Drug. Dev.*, 1997, 7:187–195.

Sumoy et al., "A role for notochord in axial vascular development revealed by analysis of phenotype and the expression of VEGR–2 in zebrafish flh and ntl mutant embryos," *Mech. Dev.*, 1997, 63:15–27.

Svoboda et al., "Selective reduction of dormant and maternal mRNAs in mouse oocytes by RNA interference," *Development*, 2000, 127:4147–4156.

Talbot and Hopkins, "Zebrafish mutations and functional analysis of the vertebrate genome," *Genes Dev.*, 2000, 14:755–762.

Tanimoto et al., "Hedgehog Creates a Gradient of DPP Activity in Drosophila Wing Imaginal Discs," *Mol. Cell*, 2000, 5:59–71.

Tavernarakis et al., "Heritable and inducible genetic interference by double–stranded RNA encoded by transgenes," *Nature Genetics*, 2000, 24:180–183.

Thompson et al., "The cloche and spadetail Genes Differentially Affect Hematopoiesis and Vasculogenesis," *Dev. Biol.*, 1998, 197:248–269.

Wallis and Muenke, "Molecular Mechanisms of Holoprosencephaly," *Mol. Genet. Metab.*, 1999, 68:126–138.

Wang et al., "A zebrafish model for hepatoerythropoietic porphyria," *Nature Genetics*, 1998, 20:239–243.

Wargelius et al., "Double–Stranded RNA Induces Specific Developmental Defects in Zebrafish Embryos," *Biochem. Biophys. Res. Commun.*, 1999, 263:156–161.

Weinberg et al., "Developmental regulation of zebrafish MyoD in wild–type, no tail and spadetail embryos," *Development*, 1996, 122:271–280.

Weinstein et al., "gridlock, a localized heritable vascular patterning defect in the zebrafish," *Nature Medicine*, 1995, 1(11):1143–1147.

Westerfield, *The Zebrafish Book: A guide for the laboratory use of zebrafish*, 3$^{rd}$ Edition, 1995, University of Oregon Press (Table of Contents only).

Wharton et al., "An activity gradient of decapentaplegic is necessary for the specification of dorsal pattern elements in the Drosophila embryo," *Development*, 1993, 117:807–822.

Wianny and Zernicka–Goetz, "Specific interference with gene function by double–stranded RNA in early mouse development," *Nature Cell Biology*, 2000, 2:70–75.

Yu et al., "Processing of the Drosophila Sog protein creates a novel BMP inhibitory activity," *Development*, 2000, 127:2143–2154.

Zernicka–Goetz, "Jumping the gun on mouse gene expression," *Nature*, 2000, 405:733.

Zhang et al., "Positional Cloning Identifies Zebrafish one–eyed pinhead as a Permissive EGP–Related Ligand Required during Gastrulation," *Cell*, 1998, 92:241–251.

Zhong et al., "gridlock, an HLH Gene Required for Assembly of the Aorta in Zebrafish," *Science*, 2000, 287:1820–1824.

Stirchak and Summerton, "Uncharged Stereoregular Nucleic Acid Analogues. 1. Synthesis of a Cytosine–Containing Oligomer with Carbamate Internucleoside Linkages," *J. Org. Chem.*, 1987, 52(19):4202–4206.

Dooley and Zon, "Zebrafish: a model system for the study of human disease," *Curr. Opn. Genet. Dev.*, 2000, 10:252–256.

Giles et al., "Antisense Morpholino Oligonucleotide Analog Induces Missplicing of C–myc mRNA," *Antisense & Nucleic Acid Drug Development*, 1999, 9:213–220.

Raz et al., "β–Lactamase as a Marker for Gene Expression in Live Zebrafish Embryos," *Dev. Biol.*, 1998, 203:290–294.

Stenkamp et al., "Function for Hedgehog Genes in Zebrafish Retinal Development," *Dev. Biol.*, 2000, 220:238–252.

Summerton and Weller, "Morpholino Antisense Oligomers: Design, Preparation, and Properties," *Antisense & Nucleic Acid Drug Development*, 1997, 7:187–195.

Summerton, "Morpholino antisense oligomers: the case for Rnase H–independent structural type," *Biochim. Biophys. Acta*, 1999, 1489:141–158.

\* cited by examiner

INHIBITION OF GENE EXPRESSION USING POLYNUCLEOTIDE ANALOGUES

CROSS REFERENCE TO RELATED APPLICATIONS

This application claims priority from U.S. Provisional Application Ser. No. 60/221,722, filed Jul. 31, 2000; U.S. Provisional Application Ser. No. 60/252,864, filed Nov. 22, 2000; and U.S. Provisional Application Ser. No. 60/284,974, filed Apr. 19, 2001.

STATEMENT AS TO FEDERALLY SPONSORED RESEARCH

Funding for the work described herein was provided by NIH grant #GM55877, which may have certain rights in the invention.

BACKGROUND

1. Technical Field

The invention relates to methods and materials involved in the determination of the function of a nucleic acid based on its sequence.

2. Background Information

The ability of the various genome projects to acquire gene sequence data has far outpaced the ability to ascribe biological functions to these new genes. This dilemma has led to the concept of "functional genomics" which can be defined as the attempt to match biological function with gene sequence on a genome scale. Since many biological processes are well conserved in evolution, model organisms for which rapid genetic tools have been developed can be used as model systems to identify human genes. For example, genes with specific biological roles are identified first in the model organism, and then genome databases are used to identify human homologues.

A useful model system for the study of vertebrate biology is the zebrafish *Danio rerio*. Aspects of the zebrafish developmental process that render the zebrafish useful as a model system include rapid development of the organ systems, transparent embryos, embryos that develop outside the womb, and availability of a large number of embryos. Furthermore, the sequence of the zebrafish genome is expected to be completed by the end of 2002. Assignment of function based on sequence information would be greatly facilitated by the development of a rapid, targeted, knockdown technology in this model vertebrate.

Recently, a number of strategies have been developed for selectively repressing the expression of specific genes. These methods are based on inducing degradation of cognate mRNAs by introduction of double-stranded RNA into cells or addition of single stranded antisense RNAs that trigger mRNA degradation by RNase H. Although these methods have been used in *D. melanogaster* and *C. elegans*, they have been unsuccessful in fish due to toxicity, nonspecific effects, or the inability to achieve uniform distribution for gene repression.

SUMMARY

The invention provides methods and materials for determining the function of a nucleic acid of known sequence. More specifically, the invention provides methods and materials for determining the function of, or a phenotype associated with, a selected nucleic acid of known sequence by specifically reducing expression from the selected nucleic acid in a teleost. The invention provides sequence specific polynucleotide analogues that can be used to specifically reduce expression from selected nucleic acids as well as methods of using sequence-specific polynucleotide analogues to reduce expression from selected nucleic acids. The function of, or phenotype associated with, a selected nucleic acid can be determined by examining morphological or other phenotypic alterations associated with the presence of a sequence-specific polynucleotide analogue in an organism.

The invention provides a teleost embryo containing a polynucleotide analogue in an amount effective to reduce expression from a selected nucleic acid in the embryo. The embryo is of a teleost species that undergoes meroblastic cleavage. The embryo can be, for example, a zebrafish embryo, a puffer fish embryo, a medaka embryo, or a stickleback embryo.

The polynucleotide analogue can be used to reduce expression from a selected nucleic acid that is an mRNA. The analogue can be complementary to a region of the mRNA that includes (1) the 5' untranslated region of the mRNA, (2) part of or the entire AUG start codon of the mRNA, (3) the coding region of the mRNA, or (4) various combinations of the above. The length of the analogue can be, for example, 9 to 90 bases in length, 15 to 50 bases in length, or 20 to 30 bases in length. The analogue can be a morpholino-modified polynucleotide, a 3'-5' phosphoroamidate, a peptide nucleic acid, or a polynucleotide containing a ribose moiety that has a 2' O-methyl group. The analogue can have at least 15% non-complementary nucleotides compared to the corresponding nucleotides in the selected nucleic acid. The analogue can be complementary to a nucleic acid in the embryo that has a homologue or orthologue in another species. The analogue can be used to reduce expression from the selected nucleic acid through larval or post-hatching stages of development.

The invention also provides for an embryo containing an exogeneous rescue mRNA that encodes a polypeptide whose expression is reduced by the polynucleotide analogue. The rescue mRNA is present in an amount sufficient for expression of the polypeptide at a level comparable to that in embryos free of the analogue.

The invention also provides for an embryo that has at least one additional polynucleotide analogue that is complementary to a different region of the same selected nucleic acid. Both analogues are present in amounts effective to reduce expression from the selected nucleic acid.

The invention also provides for an embryo that has at least one additional polynucleotide analogue that is complementary to at least one other nucleic acid that is different from the first. All analogues are present in amounts effective to reduce expression from each of the different nucleic acids.

In another embodiment, the invention provides a method for producing a teleost embryo containing a polynucleotide analogue. The embryo can be a teleost embryo that undergoes meroblastic cleavage. The analogue is present in an amount effective to reduce expression from a selected nucleic acid in the embryo. The method involves contacting the embryo, or an egg giving rise to the embryo, with the polynucleotide analogue. For example, the embryo or egg giving rise to the embryo can be injected with the analogue or the analogue can be added to the surface of the embryo or egg giving rise to the embryo. The embryo or egg giving rise to the embryo can be a zebrafish embryo or egg giving rise to the zebrafish embryo, a puffer fish embryo or egg giving rise to the puffer fish embryo, a medaka embryo or egg giving rise to the medaka embryo, or a stickleback embryo or egg giving rise to the stickleback embryo.

In another embodiment, the invention also provides a composition comprising a morpholino-modified polynucleotide that is complementary to a selected nucleic acid and a buffer having a pH similar to the physiological pH within a teleost egg or embryo. The buffer can be isotonic to the teleost egg or embryo. The buffer can be Danieau buffer. The teleost egg or embryo can be that of a species that undergoes meroblastic cleavage. The teleost egg or embryo can be a zebrafish egg or embryo, a puffer fish egg or embryo, a medaka egg or embryo, or a stickleback egg or embryo. In addition, the composition also can contain a rescue mRNA that encodes a polypeptide whose expression is reduced by the morpholino-modified analogue. The composition also can contain at least one additional polynucleotide analogue that is complementary to different regions of the selected nucleic acid.

In another embodiment, the invention provides method for determining a phenotype associated with a selected nucleic acid in a teleost embryo or egg giving rise to the embryo. The embryo or egg is that of teleost species that undergoes meroblastic cleavage. The method involves contacting the teleost embryo or egg giving rise to the embryo with a morpholino-modified polynucleotide analogue that targets the selected nucleic acid and then detecting an altered phenotype in the teleost embryo or egg, or embryo developing from said egg. The altered phenotype is one that is associated with reduced expression or altered function of said selected nucleic acid. The selected nucleic acid can be a maternal or zygotic nucleic acid and the altered phenotype can be observed from fertilization, through organogenesis, to the completion of embryogenesis.

The invention also provides a method for determining a phenotype associated with a selected nucleic acid in a teleost embryo or egg giving rise to the embryo. The embryo or egg is that of teleost species that undergoes meroblastic cleavage. The method involves contacting the teleost embryo or egg giving rise to the embryo with a morpholino-modified polynucleotide and a rescue mRNA and then detecting an altered phenotype in the teleost embryo or egg, or embryo developing from said egg. The morpholino-modified polynucleotide is present in an amount effective to reduce expression from the nucleic acid. The rescue mRNA encodes a polypeptide whose expression is reduced by the analogue and is present in an amount sufficient for expression of the polypeptide at a level comparable to that of a teleost embryo, or egg giving rise to said embryo, that is free of the analogue.

In another embodiment, the invention provides a method for determining if a phenotype mediated by a polynucleotide analogue in a teleost organism is sequence-specific. The method involves contacting a first teleost embryo or teleost egg with the polynucleotide analogue and assessing the phenotype of the first teleost embryo or egg, or a teleost embryo developing from the egg, subsequent to contacting with the polynucleotide analogue. A second teleost embryo or teleost egg is contacted with (i) the polynucleotide analogue and (ii) a rescue mRNA molecule and the phenotype of the second teleost embryo or egg, or a teleost embryo developing from the egg, is subsequently assessed. The method then involves comparing the phenotype of the first embryo or egg to the phenotype of the second embryo or egg. The analogue is sequence-specific if the phenotype of the first embryo or egg is not found in the second embryo or egg.

In another embodiment, the invention provides a method of determining if first and second polypeptides are genetic interactors. The method involves contacting a first teleost embryo or teleost egg with a first polynucleotide analogue that targets a nucleic acid encoding a first polypeptide, and assessing the phenotype of the resulting teleost embryo or egg, or a teleost embryo developing from the egg. The method also involves contacting a second teleost embryo or egg giving rise to the embryo with a second polynucleotide analogue that targets a nucleic acid encoding the second polypeptide, and assessing the phenotype of the resulting teleost embryo or egg, or a teleost embryo developing from the egg. The method also involves contacting a third teleost embryo or egg giving rise to the embryo with the first and second polynucletide analogues, and assessing the phenotype of the resulting teleost embryo or egg, or a teleost embryo developing from the egg. The phenotypes of the resulting first, second, and third teleost embryos or eggs, or teleost embryos developing from such eggs, are compared. The two polypeptides are genetic interactors if the phenotype observed in the third embryo or egg is different from the sum of the individual phenotypes observed in the first and second embryos or eggs. The phenotype observed when both polynucleotide analogues are used can be more or less extensive than the sum of the individual phenotypes observed when one of the two analogues is used.

In another embodiment, the invention provides a kit comprising a collection of different morpholino-modified polynucleotides. The different morpholino-modified polynucleotides are effective to reduce expression from different nucleic acids that are involved in a common metabolic process.

In another embodiment, the invention provides a collection of morphants, each morphant generated by a different morpholino-modified polynucleotide selected from a collection of morpholino-modified polynucleotides effective to reduce expression from different nucleic acids that are involved in a common metabolic process.

In another embodiment, the invention provides a teleost morphant defective in development of a differentiated tissue. The differentiated tissue can be pancreas, vasculature tissue, blood, eye, the central neural system, muscle, the backbone, the head, a limb, or a pigment cell.

In another embodiment, the invention provides a teleost morphant that has a phenotype characteristic of a disease condition. The disease condition can be, for example, porphyria or cyclopia.

In another embodiment, the invention provides a method of identifying a nucleic acid associated with a disease condition. The method involves generating a teleost morphant having a morphant phenotype that corresponds to a phenotype characteristic of the disease condition, and identifying the nucleic acid target of the morpholino-modified polynucleotide in the teleost morphant. The nucleic acid target of the morpholino-modified polynucleotide is a nucleic acid associated with the disease condition.

In another embodiment, the invention provides a method for assessing the effect of a drug on a morphant. The method involves contacting the morphant with the drug and assessing the phenotype of the morphant subsequent to contact with the drug. The phenotype of the morphant can be unaltered subsequent to contact with the drug or replaced by a less severe phenotype subsequent to contact with the drug. The phenotype of the morphant, subsequent to contact with said drug, can be correlated with a change in the activity of a biomarker.

In another embodiment, the invention provides a method of reducing expression from a selected nucleic acid in an animal. The method involves administering at least two polynucleotide analogues to the animal. The analogues are complementary to different regions of the selected nucleic acid. The polynucleotide analogues can act synergistically to reduce expression from the selected nucleic acid. Such expression can be reduced by a synergy factor of 3, 5, or 10. The polynucleotide analogues can be morpholino-modified polynucleotides.

In another embodiment, the invention provides a composition comprising at least two different morpholino-modified polynucleotides and a pharmaceutically acceptable carrier. The morpholino-modified polynucleotides can target the same selected nucleic acid and can be complementary to non-overlapping regions of the selected nucleic acid. The non-overlapping regions can be separated by more than 1 000 nucleotides.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
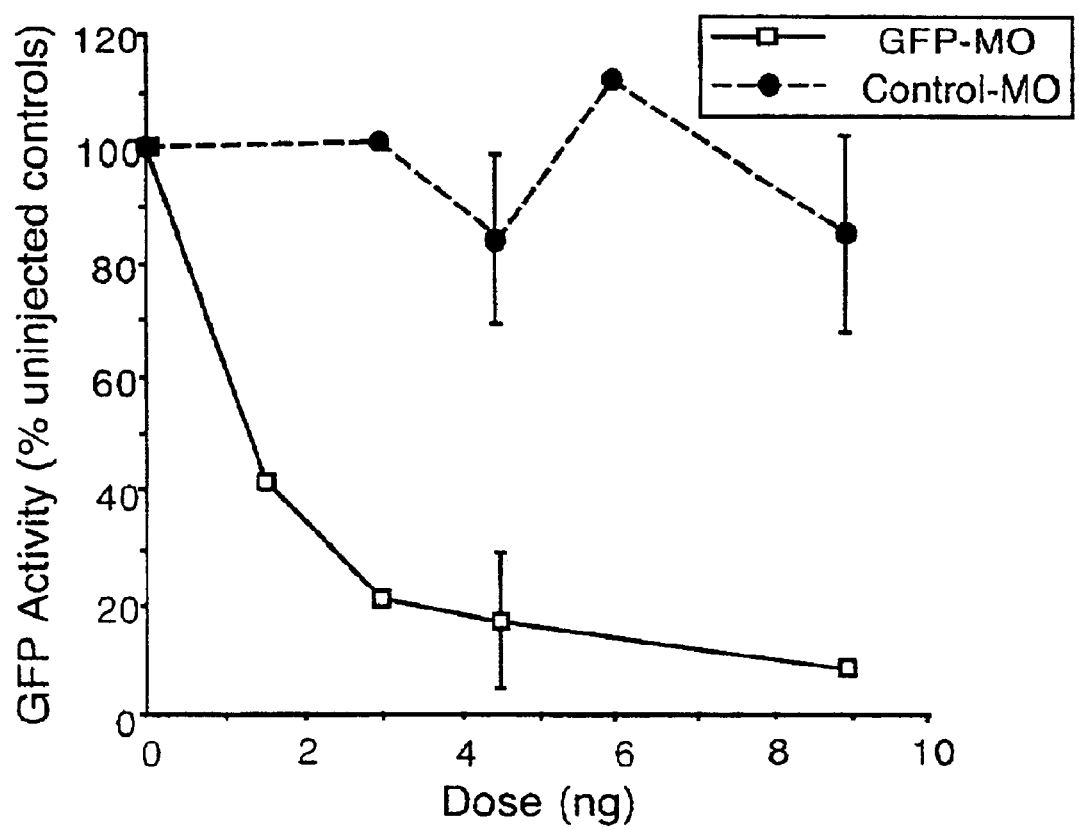
FIG. 1 is a GFP fluorescence inhibition graph demonstrating sequence-specific and dose-dependent inhibition of GFP expression.

The invention provides methods and materials for determining the function of a nucleic acid of known sequence. More specifically, the invention provides methods and materials for determining the function of, or a phenotype associated with, a selected nucleic acid of known sequence by specifically reducing expression from the selected nucleic acid in a teleost. The invention provides sequence specific polynucleotide analogues that can be used to specifically reduce expression from selected nucleic acids as well as methods of using sequence-specific polynucleotide analogues to reduce expression from selected nucleic acids. For example, the invention provides morpholino-modified polynucleotides and methods of using morpholino-modified polynucleotides for reducing expression of selected nucleic acids whose sequences are known. Reduction in expression is reflected in the level of specific RNA or polypeptide produced as well as in morphological or other phenotypic changes. The function of, or phenotype associated with, a selected nucleic acid can be determined by examining morphological or other phenotypic alterations associated with the presence of a sequence-specific polynucleotide analogue in an organism.

1. Polynucleotide and Polynucleotide Analogues

Polynucleotides are linear polymers consisting of monomeric subunits called nucleotides. A nucleotide has three components: a phosphate group, an organic base, and a five-carbon sugar that links the phosphate group and the organic base. The nucleotide subunits of a polynucleotide are linked by phophodiester bonds, i.e. the five-carbon sugar of one nucleotide forms an ester bond with the phosphate of an adjacent nucleotide. The resulting sugar-phosphates form the backbone of a polynucleotide, while the organic bases determine the sequence of the polynucleotide and allow for interaction with a second polynucleotide. When the sequence of the bases of one polynucleotide is complementary to the sequence of the bases of a second polynucleotide, the two polynucleotides can anneal to form a duplex held together by hydrogen bonds and hydrophobic interactions. Two polynucleotides are said to have complementary sequences if the bases in one polynucleotide are able to pair, through hydrogen bonding, with the bases in the second polynucleotide according to known Watson-Crick type base pairing rules, (see DNA in *Molecular Cell Biology*, Darnell et al. (1990) Scientific American Books. $2^{nd}$ Edition, pages 68–74). The strength of the interaction between the two polynucleotides is determined by the degree of complementarity. For example, the strength of interaction between two polynucleotides is greatest if the base sequences are 100% complementary. Duplexes formed between two polynucleotides with 4%, 8%, 16%, 25%, or more than 25% mismatch bases are successively less strong and will separate at successively lower temperatures. As used herein, the term "polynucleotide" refers to a DNA or an RNA polymer having at least three nucleotides.

Polynucleotide analogues are chemically modified polynucleotides. Typically, polynucleotide analogues are formed by replacing all or portions of the five-carbon sugar-phosphate backbone of a polynucleotide with alternative functional groups in such a way that base pairing with a selected nucleic acid is maintained. As used herein, the term "selected nucleic acid" refers to a DNA or an RNA having a region that is complementary to the polynucleotide analogue. The region of the selected nucleic acid that is complementary to the polynucleotide analogue can be 100% complementary or less than 100% complementary to the entire polynucleotide analogue sequence, as long as the polynucleotide analogue can anneal and form a stable duplex with the selected nucleic acid under physiological conditions. For example, a polynucleotide sequence of 25 nucleotides can have as many as three non-complementary bases distributed throughout the polynucleotide and still anneal with the selected nucleic acid.

Some examples of polynucleotide analogues include: analogues in which the bases are linked by a polyvinyl backbone (Pitha et al. (1970) *Biochem Biophys Acta* 204:39 and Pitha et al. (1970) *Biopolymers* 9: 965); peptide nucleic acids (PNAs) in which the bases are linked by amide bonds formed by pseudopeptide 2-aminoethyl-glycine groups; analogues in which the nucleoside subunits (i.e. base and sugar) are linked by methylphosphonate groups (Miller et al. (1979) *Biochem* 18: 5134; Miller et al. (1980) *J Biol Chem* 255: 6959); analogues in which the phosphate residues linking nucleoside subunits are replaced by phosphoroamidate groups (Froehler et al. (1988) *Nucleic Acids Res* 156: 4831); phosphorothioated DNAs, analogues containing sugar moieties that have 2' O-methyl groups (Cook (1998) CHAPTER 2: Antisense Medicinal Chemistry in *The Medicinal Chemistry of Oligonucleotides*. Springer, New York. pages 51–101); and morpholino-modified analogues, analogues in which the bases are linked by a morpholino-phosphorodiamidate backbone (U.S. Pat. Nos. 5,142,047 and 5,185,444). Polynucleotide analogues can be obtained commercially, produced using commercially available monomeric subunits, or synthesized using known methods. (See Braasch and Corey (2001) Chemistry and Biology, pages 1–7.)

Useful polynucleotide analogues are those that (1) can form duplexes with selected cellular nucleic acids in a sequence specific manner, (2) form duplexes that are relatively insensitive to ionic concentration or relatively resistant to cellular strand-separating mechanisms, (3) have low nuclease sensitivity, and (4) have low cellular toxicity and non-specific effects. Useful polynucleotide analogues typically are specific, can distribute uniformly throughout most or all cells of an organism, are functional in many or all cell types, are efficient at reducing expression from different nucleic acids and have little or no non-specific effects. Furthermore, the technique for use is straightforward to perform and reproducible.

Typically, useful polynucleotide analogues are single stranded, and can be various lengths such as 8 to more than 112 bases in length. Polynucleotide analogues can be 12 to 72 bases in length. For example, polynucleotide analogues can be 15 to 45 bases in length. Ideally, polynucleotide analogues are 18–30 bases in length.

A useful polynucleotide analogue can be complementary to a sense or an antisense nucleic acid. When complementary to a sense nucleic acid, the polynucleotide analogue is said to be antisense. When complementary to an antisense nucleic acid, the analogue is said to be sense. The nucleic acid can be RNA (e.g. a pre-mRNA or an mRNA) or DNA. For example, a useful polynucleotide analogue can be antisense to a pre-mRNA or an mRNA moleculeor sense to the DNA molecule from which an mRNA is transcribed.

A useful polynucleotide analogue can be complementary to the non-coding region of a nucleic acid. A non-coding region, for example, can be a region upstream of a transcriptional start point or a region downstream of a transcriptional end-point in a DNA molecule. A non-coding region also can be a region upstream of the translational start codon or downstream of the stop codon in a pre-mRNA or an mRNA molecule. A non-coding region also can be the intronic sequences within a pre-mRNA (see Ekker & Larson (2001) *Genesis* 30:89–93). Furthermore, a useful polynucleotide analogue can be complementary to the coding region of a pre-mRNA molecule or an mRNA molecule, or the region corresponding to the coding region on the antisense DNA strand. As used herein, the term "coding sequence" refers to the region of DNA or RNA that encodes an RNA molecule or a polypeptide having a cellular function. A useful polynucleotide analogue also can be complementary to both coding and non-coding regions of a selected nucleic acid. A polynucleotide analogue that is complementary to both coding and non-coding regions of a selected nucleic acid, for example, is one that is complementary to a region that includes a portion of the 5' untranslated region leading up to the start codon, the start codon, and coding sequences immediately following the start codon of a selected mRNA. A polynucleotide analogue that is complementary to both coding and non-coding regions of a selected nucleic acid also includes one that is complementary an intron/exon junction of a selected pre-mRNA molecule (see Ekker & Larson (2001) *Genesis* 30:89–93).

2. Reduction of Expression

A polynucleotide analogue can be used to reduce expression from a selected nucleic acid of known sequence. As used herein, "reduction" or "reduce" with respect to expression from a nucleic acid refers to a decrease in expression, or to decrease expression, in an amount that can be detected by assessing changes in RNA level, protein level, and phenotype. For example, reduction can refer to a 5%, 10%, 25%, 50%, 75%, or more than 75% decrease in expression. A reduction in expression also includes complete inhibition of expression, whereby greater than 95% reduction of expression from a nucleic acid is achieved.

As used herein, the term "expression," with respect to expression of a gene or expression from a nucleic acid, refers to production of a functional RNA molecule from a DNA molecule as well as production of a functional polypeptide from an mRNA molecule. Expression from a selected nucleic acid can be examined using standard methods known in the art. For example, RNA levels can be determined by Northern hybridization and in situ hybridization using the appropriate nucleic acid hybridization probes, while polypeptide levels can be determine by antibody staining and western hybridization. Development of organs, differentiated tissues, and other cellular structures that are affected by reduction in expression of selected nucleic acids can be assessed using various methods. For example, vasculature can be visualized with FITC-dextran injections; cartilage can be visualized using Alcian Blue staining; and muscles can be visualized using fluorescent-phalloidin staining. Alternatively, the expression of tissue-specific genes can be used to assess development of organs, differentiated tissues, and particular cellular structures. For example, expression of a thymus specific marker such as Rag-1 can be used to assess thymus development; and expression of pancreas-specific markers such as Fspondin and islet-1 can be used to assess pancreas development. (For standard methodologies, see H. W. Detrich III, M. Westerfield, and L. I. Zon, *Methods in Cell Biology* Vol. 59: The Zebrafish Biology, Academic Press. San Diego) Expression from a nucleic acid can be reduced by interfering with (1) any process necessary for RNA transcription, (2) RNA processing, (3) RNA transport across the nuclear membrane, (4) any process necessary for RNA translation, or (5) RNA degradation.

Expression from a nucleic acid such as a DNA molecule can be reduced by interfering with processes necessary for formation of a functional RNA molecule or transport of the RNA into the cytoplasm. Processes necessary for formation of a functional RNA molecule include, for example, RNA polymerase binding to promoter regions, binding of transcriptional activator to its recognition sequence, and transcription. A polynucleotide analogue that anneals to DNA and interferes with processes necessary for formation of a functional RNA molecule generally, though not necessarily, has a sequence that is complementary to the antisense DNA strand from which mRNA is transcribed. Such polynucleotide analogues are referred to as "antigene" molecules.

Expression from a nucleic acid such as an RNA molecule can be reduced by interfering with any process necessary for formation of a functional RNA molecule or proper translation of an mRNA molecule into a functional polypeptide. Expression from an RNA molecule, for example, can be reduced by interfering with RNA processing, ribosome binding to the ribosome-binding site of mRNAs, interfering with initiation of translation, interfering with the translation process, or interfering with proper termination of translation (see Ekker and Larson (2001) *Genesis* 30:89–93 and Nasevicius & Ekker (2001) *Curr Opin in Mol Therapeutics* 3:224). A polynucleotide analogue that anneals to a region of an mRNA molecule and interferes with translation has a sequence that is complementary to that region of the mRNA molecule and is referred to as an antisense molecule. Antisense molecules, for example, can bind and sterically inhibit scanning of the mRNA by the 40s ribosomal subunit. Antisense molecules also can reduce expression by inducing the cellular nuclease system that degrades cognate mRNAs. In the RNaseH dependent mechanism, the double stranded mRNA/antisense RNA that is formed is degraded by RNaseH.

Reduction of expression from a selected nucleic acid can be achieved using one polynucleotide analogue. Reduction of expression from a selected nucleic acid also can be achieved using two or more polynucleotide analogues that are complementary to different regions of the same selected nucleic acid. When two or more polynucleotide analogues are used to reduce expression from a selected nucleic acid, the polynucleotide analogues can be complementary to non-overlapping regions or to overlapping regions of the selected nucleic acid. When non-overlapping, polynucleotide analogues can be complementary to regions of the selected nucleic acid that are 0, 1, 2, 5, 10, 25, 50, 100, 500, 1000, or more than 1000 nucleotides apart.

When two or more polynucleotide analogues are used to reduce expression from a selected nucleic acid, the two or more polynucleotide analogues can have an additive or synergistic effect on the phenotype of the organism. A phenotype that results from introduction of polynucleotide analogues into a selected organism is herein referred to as a phenotype mediated by the polynucleotide analogues. The effect of two or more analogues can be described as additive or synergistic based, for example, on the penetrance frequency of a phenotype mediated by the analogues. The penetrance frequency used to determine whether the effect of two or more analogues is additive or synergistic is the frequency determined for a 1× dose of each polynucleotide analogue used. As used herein, penetrance frequency is the percent of organisms exhibiting a particular phenotype when contacted with a particular analogue. For example, if 100 organisms are contacted with analogue-1 and 80 of these exhibit phenotype-1, then the penetrance frequency is 80%. A 1× dose of an analogue can be any amount needed to achieve a penetrance frequency of less than 50%. To determine a 1× dose for an analogue, a dose response curve is generated for each analogue of interest. From the dose response curve, any amount of an analogue that results in a penetrance frequency less than 50% and with minimal toxic effects can be used as the 1× dose. Two analogues are considered to have an additive effect if the penetrance frequency, obtained when both analogues are used, each at 1× dose, is equal to the sum of the penetrance frequencies of individual analogues at 1× doses. For example, two analogues are considered to have an additive effect if the penetrance frequencies are (1) 10% for a 1× dose of analogue-1, (2) 20% for a 1× dose of analogue-2, and (3) 30% for a 1× dose of analogue-1 and a 1× dose of analogue-2 when used together. In contrast, two analogues are considered to have a synergistic effect if the penetrance frequency, obtained when both analogues are used, each at 1× dose, is greater than the sum of the penetrance frequencies of individual analogues at 1× doses. For example, two analogues are considered to have a synergistic effect if the penetrance frequencies are (1) 10% for a 1× dose of analogue-1, (2) 20% for a 1× dose of analogue-2, and (3) 90% for a 1× dose of analogue-1 and a 1× dose of analogue-2 when used together.

The effect of two or more analogues also can be described as, without limitation, additive or synergistic based on the severity of the phenotype mediated by the analogues compared to "the sum of the individual phenotypes" mediated by each of the analogue used. A phenotype that is "the sum of individual phenotypes" is one that results from an additive effect of each analogue. Two or more analogues are considered to have a synergistic effect if the phenotype mediated by the analogues is more severe than "the sum of the individual phenotypes." For example, two analogues are considered to have a synergistic effect if (1) 100% of the organisms contacted with analogue-1 exhibit a 10% reduction in blood vessel formation, (2) 100% of the organisms contacted with analogue-2 exhibit a 20% reduction in blood vessel formation, and (3) 100% of organisms contacted with analogue-1 and analogue-2 exhibit a 90% reduction in blood vessel formation. In this example, the percent of reduction in blood vessel formation is the severity of the phenotype mediated by the polynucleotide analogues. In contrast, two analogues are considered to have an additive effect on the phenotype of an organism if the phenotype mediated by the analogues is not more severe than "the sum of the individual phenotypes." For example, two analogues are considered to have a synergistic effect if (1) 100% of the organisms contacted with analogue-1exhibit a 10% reduction in blood vessel formation, (2) 100% of the organisms contacted with analogue-2 exhibit a 20% reduction in blood vessel formation, and (3) 100% of organisms contacted with analogue-1 and analogue-2 exhibit a 30% reduction in blood vessel formation.

Phenotype severity can, in some instances, be measured by the extent of reduction in expression from the nucleic acid targeted by the analogues. The amount of reduction in expression can be quantitated by standard methodologies and then compared to determine whether two or more analogues have an additive or synergistic effect on reduction of expression.

A useful measure of the synergy of two analogues is the synergy factor. As used herein, the term "synergy factor" is defined as the penetrance frequency, or the severity of the phenotype, observed for two or more analogues divided by the expected additive penetrance frequency or "sum of the individual phenotypes," respectively. The synergy factor can be determined by comparing the actual penetrance frequency obtained when both analogues are used (each at 1× dose) with the penetrance frequency expected of an additive effect. For example, the synergy factor is 3 (90%/30%) if the penetrance frequencies are (1) 10% for a 1× dose of analogue-1, (2) 20% for a 1× dose of analogue-2, and (3)

90% for a 1× dose of analogue-1 and a 1× dose of analogue-2 when used together. The synergy factor also can be determined by comparing the severity of the phenotype observed with "the sum of the individual phenotypes" when two or more analogues are used. For example, the synergy factor also is 3 (90%/30%) if (1) 10% reduction in blood vessel formation is observed in 100% of the organisms contacted with analogue-1, (2) 20% reduction in blood vessel formation is observed in 100% of the organisms contacted with analogue-2, and (3) 90% reduction in blood vessel formation is observed in 100% of organisms contacted with analogue-1 and analogue-2 together. A synergy factor can be determined for two or more polynucleotide analogues. For example, a synergy factor can be determined for two, three, or more than three analogues. A synergy factor can be any value greater than 0. For example, a synergy factor can be 0.2, 0.4, 0.8, 1.5, 2, 4, 6, 8, 10, 15, 20, or more than 20. A synergistic effect is indicated when the synergy factor for a particular group of analogues has a value greater than 1, for example, 1.2, 1.5, 1.8, 2.1, 5, 10, 20, or more than 20. A synergy factor of 1 represents an additive effect. Synergy factors between 0 and 1 indicate an interference effect.

Polynucleotide analogues also can be used to reduce expression from two or more different selected nucleic acids in an organism. For example, multiple polynucleotide analogues, i.e. at least two, having sequences complementary to multiple selected nucleic acids can be used to reduce expression from the selected nucleic acids. When two or more polynucleotide analogues are used to reduce expression from two or more nucleic acids, reduction in expression of the various nucleic acids can result in phenotypes of two classes. The first class is representative of "the sum of the individual phenotypes" mediated by each of the analogues used, while the second class consists of those phenotypes that do not fall into the first class. A phenotype that is "the sum of individual phenotypes" is one that results from an additive effect of each analogue. The additive effect of multiple polynucleotide analogues is as described for multiple polynucleotide analogues that target one selected nucleic acid. An organism that has been contacted with two or more analogues also is described as having a phenotype that is "the sum of individual phenotypes" if the individual phenotype mediated by each analogue is distinct and present in that organism. Alternatively, organisms that have been contacted with two or more analogues can exhibit phenotypes that are not considered "the sum of individual phenotypes." These organisms exhibit phenotypes that are more or less extensive than, or distinctly different from, a phenotype that is "the sum of individual phenotypes." Typically, phenotypes that are not "the sum of individual phenotypes" represent synergistic or interference effects of multiple analogues.

To be considered additive, synergistic, interference, one that represents "the sum of other phenotypes," or one that is distinctly different from a phenotype that is the "sum of individual phenotypes," a phenotype mediated by a polynucleotide analogue must be sequence-specific, i.e., the phenotype must result from sequence-specific reduction of expression from a selected nucleic acid.

3. Determination of Sequence-specific Reduction of Expression

A phenotype mediated by a polynucleotide analogue is said to be "sequence-specific" if the phenotype is primarily or exclusively associated with, or results from, reduction of expression from the selected nucleic acid. To determine if a phenotype mediated by a polynucleotide analogue is sequence-specific, a second polynucleotide analogue of unrelated sequence that targets the same nucleic acid can be used. Alternatively, a control polynucleotide analogue that does not target the same nucleic acid or a rescue mRNA that compensates for the reduction in expression from the selected nucleic acid can be used.

To show that a phenotype mediated by a first polynucleotide analogue is sequence-specific, a second polynucleotide analogue that also targets the same selected nucleic acid is introduced into a model organism. A phenotype mediated by the second polynucleotide analogue that is the same as the phenotype mediated by the first polynucleotide analogue indicates that the phenotype mediated by either polynucleotide analogue is sequence-specific.

Alternatively, a control polynucleotide analogue also can be used to confirm that a phenotype mediated by a first polynucleotide analogue is sequence-specific. A control polynucleotide analogue is somewhat similar in sequence to the first polynucleotide analogue. The control polynucleotide analogue, however, has a number of bases that are dissimilar to the first polynucleotide analogue such that the control polynucleotide analogue is not sufficiently complementary and so will not anneal to the selected nucleic acid targeted by the first polynucleotide analogue. Therefore, no phenotype mediated by a control polynucleotide analogue is observed. A phenotype mediated by the first polynucleotide analogue that is not observed when the control polynucleotide analogue is used indicates that the phenotype mediated by the first polynucleotide analogue is sequence-specific. If a phenotype mediated by the control polynucleotide analogue is observed, then the phenotype mediated by the first polynucleotide analogue cannot be concluded to be sequence-specific.

In addition, a rescue mRNA encoding the polypeptide whose expression is reduced by a polynucleotide analogue can be used to show that a phenotype mediated by the polynucleotide analogue is sequence-specific. The rescue mRNA is introduced into the organism exhibiting the phenotype mediated by the polynucleotide analogue. Restoration of a wild type phenotype in place of the phenotype mediated by the polynucleotide analogue indicates that the phenotype mediated by the polynucleotide analogue is sequence-specific. A phenotype mediated by a morpholino-modified polynucleotide analogue that has been confirmed to be sequence-specific by a rescue mRNA or targeting with a second morpholino of unrelated sequence is referred to as a morphant phenotype. As used herein, the term "morphant" refers to an organism exhibiting a sequence-specific phenotype mediated by a morpholino-modified polynucleotide analogue.

4. Applications of Polynucleotide Analogues

Polynucleotide analogues can be used to determine the function of a coding sequence of, or a phenotype associated with, a selected nucleic acid of known sequence. Nucleic acids can be maternal or zygotic nucleic acids and can be involved in any biological process, for example embryogenesis and development, gene expression, regulation of gene expression, formation of particular differentiated tissues, cell signaling, and metabolic processes necessary for (1) embryogenesis and development, (2) gene expression and its regulation, (3) formation of differentiated tissues, and (4) cell signaling. Nucleic acids of interest also are those associated with a disease condition. A nucleic acid that is associated with a disease condition can be one in which reduction in expression leads to a disease condition or alleviates a disease condition. A disease condition can result from any change, for example an increase or decrease, in the level of a biomarker such as a polypeptide, a nucleic acid, a lipid, any intracellular or exocellular molecule or compound, and the phophorylated and unphosphorylated forms of a cellular molecule. A disease condition can result from, for example, excessive expression of a nucleic acid or expression of a mutated form of a nucleic acid thereby forming a product with aberrant activity.

To determine the function of the coding sequence of, or phenotype associated with, a selected nucleic acid of known sequence, a polynucleotide analogue is synthesized having a sequence complementary to the sequence of the selected nucleic acid. A polynucleotide analogue designed to have a sequence that is complementary to the sequence of a selected nucleic acid is said to "target" the selected nucleic acid. When the polynucleotide analogue is introduced into an organism, effects of the polynucleotide analogue on expression from the selected nucleic acid as well as associated phenotypes are examined.

Organisms useful for functional studies with polynucleotide analogues are those in which a polynucleotide analogue is able to distribute uniformly and inhibit expression from a selected nucleic acid in cells that express the selected nucleic acid. Organisms can be a fertilized or unfertilized egg, a cell in culture, an embryo, or a juvenile or an adult animal. An animal, for example, can be a fish, a frog, a mouse, a guinea pig, a sheep, a chimpanzee, or a human. Vertebrate organisms such as teleost eggs and embryos that undergo meroblastic cleavage can be used for functional studies with polynucleotide analogues. Cleavage refers to a series of mitotic divisions that occur in rapid succession as a fertilized egg is transformed into a multicellular embryo. The multicellular embryo consists of smaller nucleated cells referred to as blastomeres. In meroblastic cleavage, only a part of the egg is subdivided into blastomeres, in contrast to organisms that undergo holoblastic cleavage in which the entire egg is subdivided into blastomeres. The blastomeres generated from meroblastic cleavage are continuous with the remaining uncleaved cytoplasm of the egg (see Balinsky et al. (1981) Cleavage in *An Introduction to Embryology*, 5$^{th}$ Edt. CBS College Publishing, pages 135–152). Examples of vertebrate organisms that undergo meroblastic cleavage, and therefore are useful model organisms for nucleic acid functional studies using polynucleotide analogues include the eggs and embryos of a zebrafish, a medaka, a pufferfish, and a stickleback.

Polynucleotide analogues can be used to determine the function of, or phenotype associated with, any nucleic acid of known sequence but unknown function. The nucleic acid can be one that is present, or one that is not present, in the model organism. To determine the function of, or phenotype associated with, any nucleic acid of known sequence but unknown function, the sequence of a homologue, orthologue, or paralogue that is present in the model organism is used. Homologues refer to nucleic acids encoding polypeptides having similar domains or structures that can be identified by nucleotide or amino acid sequence comparison. Homologues also can have similar activities. Orthologues refer to homologues that are from different species, while paralogues refer to homologues within one organism that have distinct expression patterns and therefore distinct biological roles. From the known sequence of a homologue, orthologue, or paralogue, a polynucleotide analogue targeting the homologue, orthologue, or paralogue is generated. The polynucleotide analogue targeting the homologue, orthologue, or paralogue is introduced into the model organism and the organism is assessed for a phenotype associated with reduction of expression of the homologue, paralogue, or orthologue. From the phenotype observed, the function of the homologue, paralogue, or orthologue can be determined, and in turn, the function of the newly discovered nucleic acid or its involvement in a particular aspect of the biology of the organism can be inferred.

Polynucleotide analogues also can be used to determine whether two nucleic acids are, or encode, genetic interactors. As used herein, the term "genetic interactors" refers to nucleic acids or polypeptides that function in a common metabolic process. As used herein, the term "metabolic process" refers to particular sets of metabolic processes involved in (1) embryogenesis and development, (2) gene expression and its regulation, (3) formation of differentiated tissues, (4) cell signaling, and (5) any other cellular and physiological processes. Genetic interactors, for example, can be nucleic acids such as DNA or RNA, or the polypeptides encoded by nucleic acids. Genetic interactors can interact directly or indirectly.

To determine if two different nucleic acids are, or encode, genetic interactors, polynucleotide analogues that target the two nucleic acids can be used to reduce expression from the nucleic acids. A sequence-specific phenotype mediated by both polynucleotide analogues is compared to sequence-specific phenotypes mediated by each of the polynucleotide analogues. If the two different nucleic acids are genetic interactors, the phenotype mediated by both analogues is expected to be different than the "sum of the individual phenotypes" mediated by each of the analogues. That is, if the targeted nucleic acids encode two polypeptides that are genetic interactors, reduction in expression from both nucleic acids in an organism will result in either a synergistic effect on the phenotype mediated by the individual nucleic acids or a phenotype that is distinctly different from the "sum of the individual phenotypes." In contrast, the targeted nucleic acids encode two polypeptides that are not genetic interactors if reductions in expression from both nucleic acids give rise to a phenotype that is "the sum of the individual phenotypes."

Similarly, polynucleotide analogues also can be used to generate model organisms for the study of diseases. Disease conditions associated with loss or reduction of function of a particular nucleic acid in a higher organism such as a human can be generated in a model organism using a polynucleotide analogue if the model organism has a homologous or orthologous nucleic acid. For example, a polynucleotide analogue that targets the homologue or orthologue in the model organism is generated and introduced into the model organism. Reduction in expression of the homologue or orthologue results in a morphant organism that exhibits the disease condition. Morphants exhibiting a disease condition can be used to screen for compounds that are useful for treating the disease condition or alleviating the severity of the disease condition. To screen for compounds that are useful for treating a disease condition or alleviating the severity of the disease condition, morphants exhibiting the disease condition can be contacted with candidate compounds and then assessed to determine whether the disease condition is lessened.

Polynucleotide analogues also can be used to identify nucleic acids not known to be associated with a disease condition. To identify nucleic acids not known to be associated with a disease condition, various polynucleotide analogues are introduced into wild type organisms and morphants exhibiting any particular disease condition are chosen for further analysis. A collection of polynucleotide analogues, for example, can be used to generate a collection of morphants. Those morphants that exhibit a particular disease condition can be used to identify drug targets as well as to develop novel treatments for the disease condition. A potential drug target, for example, is identified as the nucleic acid whose reduction in expression led to the disease condition. A morphant that exhibits a particular disease condition can be used to screen for novel treatments for the particular disease condition as described earlier.

To identify nucleic acids whose excessive activity leads to a disease condition, polynucleotide analogues are introduced into organisms exhibiting the disease condition. Those organisms whose disease state is lessened by the polynucleotide analogue are further examined to identify nucleic acids whose expressions have been reduced. These nucleic acids are identified as useful targets for the development of novel treatments for the particular disease.

Polynucleotide analogues also can be used therapeutically as treatments for disease conditions. For example, a polynucleotide analogue can be used to treat disease conditions associated with excessive expression of a particular nucleic acid or expression of a culprit nucleic acid. Multiple polynucleotide analogues, for example, that target the same culprit nucleic acid and have synergistic effects in alleviating the disease phenotype can be useful for circumventing toxicity associated with treatment using one analogue, since lower amounts of analogues can be used.

5. The Morpholino-modified Polynucleotide Analogue/Zebrafish System

An example of a system that is useful for determining function or phenotype associated with a selected nucleic acid of known sequence is the morpholino-modified polynucleotide analogue/zebrafish system.

Morpholinos (morpholino-modified polynucleotide analogues) are not subjected to any known endogenous enzymatic degradation activity. Morpholinos have been shown to bind to and block translation of mRNA both in vitro and in tissue culture (Summerton (1990) *Biochim Biophys Acta* 1489:141–158; Summerton and Weller (1997) *Antisense Nucleic Acid Drug Dev* 7:187–195). This approach makes morpholino targeting highly predictable for polynucleotide design and significantly reduces non-specific effects. In contrast, traditional antisense polynucleotide approaches utilize RNAse-H-based degradation of mRNA as a mechanism of action. RNAse-H mediated strategies, however, have been tried with only modest success (Barabino et al. (1997) *Mech Dev* 63:133–143). Furthermore, in fish, single stranded polynucleotides tend to be toxic or there is an inability to achieve uniform distribution among all cells of the organism.

In the following sections, the examples describing the use of morpholinos in zebrafish show these compounds to be (1) sequence specific and (2) extremely potent in all cells for at least the first 50 hours of development in F0 zebrafish embryos as targeted gene 'knockdown' agents. This period in the zebrafish embryonic development includes the fundamental vertebrate processes of segmentation and organogenesis. This tool offers the opportunity to pursue sequence-specific gene targeting studies without the necessity of laborious, time consuming, and expensive F3 vertebrate genetic testing. Morpholinos, thus, offer a high throughput F0 vertebrate assay system for vertebrate functional genomics applications.

The use of morpholino-based gene targeting represents a new tool in the genetic repertoire of vertebrate biologists and, combined with the excellent embryology of the zebrafish, is extremely powerful in the elaboration of gene function for similarly conserved developmental processes.

6. Methods of Administration

Polynucleotide analogues can be introduced into a model organism by methods used to introduce single stranded mRNA into the model organism. (See Hyatt and Ekker (1999) Methods in Cell biology 59:117–126). Examples of delivery methods include (1) microinjection and (2) simply exposing the model organism to the polynucleotide analogue. Polynucleotide analogues can be delivered in water or a suitable buffer. A suitable buffer is one in which the polynucleotide analogue can be dissolved and that is non-toxic to the model organism to which the polynucleotide analogue is to be delivered. A non-toxic buffer can be one that is isotonic to, or one that has a pH similar to the physiological pH of, an organism to which the polynucleotide analogue is to be delivered. A buffer that is isotonic with an organism is one that has the same osmolarity as the organism. Danieau solution, for example, is isotonic with the model organism zebrafish. A pH similar to the physiological pH of the organism can be 2.5 pH units below or above the pH of the organism. A polynucleotide solution prepared for delivery into zebrafish, for example, can have a pH that is 5, 5.4, 5.7, 6, 6.2, 6.6, 7, 7.4, 7.8, 8, 8.6, or any value in between these.

Different polynucleotide analogues can be introduced into the model organism as a mixture. Alternatively, different polynucleotide analogues can be introduced sequentially by multiple exposures or injections.

7. Compositions and Kits

The invention provides compositions of individual polynucleotide analogues in a suitable buffer. The invention also provides for compositions of at least two polynucleotide analogues in a pharmaceutically acceptable carrier.

Compositions can be in the form of tablets, capsules, powders, solutions, suspensions, or emulsions depending on the route of administration. Compositions can contain sterile pharmaceutically acceptable carriers or excipients. Common pharmaceutically acceptable carriers or excipients can be aqueous or non-aqueous. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives, flavorings, sugars, and other additives such as antimicrobials, antioxidants, chelating agents, inert gases, and the like also may be present.

For administration by injection, a solution can be prepared using a suitable non-toxic buffer, i.e. one that is similar in pH, is isotonic, or both similar in pH and isotonic, to a selected organism.

For oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration also can be formulated to give controlled release of a polynucleotide analogue. Biocompatible, biodegradable lactide polymer, lactide/glycolide copolymer, or polyoxethylene-polyoxypropylene copolymers are examples of excipients for controlling the release of a polynucleotide analogue of the invention in vivo.

For nasal administration, preparations can be in the form of a liquid solution, a gel, or a dry product. Inhalation formulations may be aqueous solutions containing, for example, polyoxyethylene-9-lauryl ether, glycocholate and deoxycholate, and may contain excipients such as lactose, if desired. Nebulised aqueous suspensions or solutions can include carriers or excipients to adjust pH and/or tonicity. Nasal drops can be administered in the form of oily solutions.

For parenteral administration, liquid solutions or suspensions in aqueous physiological buffer solutions can be prepared as desired using standard methods. Formulations may contain common excipients as well as glycocholate for buccal administration. Suitable parenteral delivery systems include ethylene-vinyl acetate copolymer particles, osmotic pumps, implantable infusion systems, and liposomes.

The invention also provides kits comprising a collection of different polynucleotide analogues, for example, morpholino-modified polynucleotides. The collection of polynucleotide analogues can be analogues directed to nucleic acids of the entire genome of an organism. The collection of polynucleotide analogues also can be directed to nucleic acids involved in a common biological process such as, for example, a disease condition, regulation of nucleic acid expression, or a common metabolic, developmental, or signaling pathway.

The invention also provides a collection of morphants that can be generated using the collection of different polynucleotide analogues. Morphants can be models of human diseases such as prophyria or cyclopia. Morphants also can be defective in a differentiated tissue, for example, vasculature, blood, an organ, or a specialized cell type such as fibroblasts, neurons, and epithelial cells.

The invention will be further described in the following examples, which do not limit the scope of the invention described in the claims.

EXAMPLES

Example 1

Zebrafish Care and Egg Collection

Standard zebrafish care protocols are described in Westerfield (1995) *The Zebrafish Book: A Guide for the Laboratory Use of Zebrafish (Brachydanio rerio)* 3$^{rd}$ Edition, University of Oregon Press.

Zebrafish were kept in 6.5 gallon (26 liters) and 20 gallon (76 liters) plastic tanks at 28° C. A 6.5 gallon tank housed 25 fish and a 20 gallon tank housed 70 fish. Tank water was constantly changed with carbon-filtered and UV-sterilized tap water (system water) at a rate of 15 to 40 mL/min. Alternatively, tank water was replaced each day by siphoning up debris from the bottom of the tank. Tap water, aged a day or more in an open (heated) tank to release chlorine, was adequate. More consistent conditions, however, were obtained by adding commercial sea salts to deionized or distilled water (60 mg of 'Instant Ocean' salt per liter of water, see Westerfield (1995) *The Zebrafish Book: A Guide for the Laboratory Use of Zebrafish (Brachydanio rerio)* 3$^{rd}$ Edition, University of Oregon Press). A 10-hour dark and 14-hour light day cycle was maintained in zebrafish facility.

Fish were fed brine shrimp twice a day. To make shrimp, 100 mL of brine shrimp eggs were added to 18 L of salt water (400 mL of 'Instant Ocean' salt per 18 L of water) and aerated vigorously. After 2 days at 28° C., the shrimp were filtered through a fine net, washed with system water, suspended in system water, and fed to fish. Alternatively, fish could also be fed with 'Tetra' brand dry flake food.

Zebrafish spawning was induced every morning shortly after sunrise. To collect the eggs, a 'false bottom container' system was used (Westerfield (1995) *The Zebrafish Book: A Guide for the Laboratory Use of Zebrafish (Brachydanio rerio)* 3$^{rd}$ Edition, University of Oregon Press). The system consisted of two containers of approximately 1.5 L, one slightly smaller than the other. The bottom of the smaller container was replaced with a stainless steel mesh with holes bigger than the diameter of zebrafish eggs. The smaller container was then placed into the bigger container, and the setup was filled with system water. Up to eight zebrafish were placed inside the smaller container. When the fish spawn, the eggs fall through the mesh into the bigger container, and in this way, the eggs cannot be reached by the fish and eaten. About 10–15 minutes were allowed for spawning, after which time the smaller container with the fish was transferred into another bigger container. The eggs were collected by filtering using a mesh with the holes smaller than the diameter of the eggs. Fish were used once a week for optimal embryo production.

Example 2

Zebrafish and *Xenopus* Strains

The zebrafish E-line transgenic line contained a single copy of the pT-EF1α-GFP-pA transposon at the E-line locus (Nasevicius and Ekker (2000) *Nature Genetics* 26:216–220). Heterozygous E-line embryos were obtained from an outcross of homozygous E-line adults and can be obtained S. C. Ekker, University of Minnesota Medical School, Minneapolis, Minn.

Example 3

Polynucleotide Analogues

Morpholino phosphorodiamidates antisense oligonucleotides (morpholinos or MOs) were purchased from Gene-Tools, LLC (Corvallis, Oreg.). MO sequences were designed based on parameters recommended by the company. MOs were 21 to 25-bases in length, had no predicted internal hairpins, and consisted of approximately 50% G/C and 50% A/T residues. Sequences having four consecutive G nucleotides were avoided. All MOs were designed to bind to 5' untranslated regions (UTRs), or regions flanking and including sequence encoding the initiating methionine.

FITC-labeled 14-mer peptide nucleic acids (PNAs) were obtained from Applied Biosystems. Rhodamine-labeled 25-mer PNAs were a gift from Dr. D. Corey, University of Texas Southwestern. 2'-O methyl RNAs were obtained from Integrated DNA Technologies, Inc. Phosphoramidates were obtained from Annovis, Inc.

Solutions of polynucleotide analogues were prepared and injected as described in Example 4.

Sequences of the polynucleotide analogues used were as follows. Residues complementary to the predicted start codon are underlined in all cases.

FITC-labeled MO and FITC-labeled 3'-5' phosphoroamidate:
  5'-ATC CAC AGC AGC CCC TCC ATC ATC C-3' (SEQ ID NO: 1)
FITC-labeled 2'-O methyl RNA:
  5'-AUC CAC AGC AGC CCC UCC AUC AUC C-3' (SEQ ID NO: 25)
FITC-labeled PNA-1: 5'-AGC AGC CCC TCC AT-3' (SEQ ID NO: 2)
FITC-labeled PNA-2: 5'-TCTCTCTC-O-nJTJTJTJT-3' (SEQ ID NO: 3)
Negative control-MO sequence [unlabeled or FITC-labeled at the 3' end]:

5'-CCTCTTACCTCAGTTACAATTTATA-3' (SEQ ID NO: 4)
chordin-MO [FITC-labeled at the 3' end] and chordin-PNA [rhodamine-labeled]:
  5' ATCCACAGCAGCCCCTC<u>CAT</u>CATCC-3' (SEQ ID NO: 5)
GFP-MO:   5'-TCTTCTCCTTTACT<u>CAT</u>TTTCTACC-3' (SEQ ID NO: 6)
GFPD4-MO:   5'-TCTaCTCgTTTACT<u>CAT</u>TaTCTtCC-3' (SEQ ID NO: 7)
oep-MO: 5'-GCCAATAAACTCCAAAACAACTCGA-3' (SEQ ID NO: 8)
ntl-MO:   5'-GACTTGAGGCAGG<u>CAT</u>ATTTCCGAT-3' (SEQ ID NO: 9)
shh-MO #1: 5'-CAGCACTCTCGTCAAAAGCCG<u>CAT</u>T-3' (SEQ ID NO: 10)
shh-MO #2: 5'-TGTCTAGCAGGGTTTCTCGTTGTCG-3' (SEQ ID NO: 11)
twhh-MO:   5'-TTC<u>CAT</u>GACGTTTGAATTATCTCTT-3' (SEQ ID NO: 12) nacre-MO and nacre-PNA [rhodamine-labeled]:
  5'-<u>CAT</u>GTTCAACTATGTGTTAGCTTCA-3' (SEQ ID NO: 13)
sparse-MO: 5'-TATAAGTCCATCTATCTCATGTGTG-3' (SEQ ID NO: 14)
urod-MO:   5'-GAATGAAACTGTCCTTATCCAT<u>CA</u>-3' (SEQ ID NO: 15)
VEGF-A-1: 5'-GTATCAAATAAACAACCAAGTT<u>CAT</u>-3' (SEQ ID NO: 16)
VEGF-A-1D4 [four base mismatch]:
  5'-GTAaCAAtTAAACAACCAtGTTgAT-3' (SEQ ID NO: 17)
VEGF-A-3: 5'-TAAGAAAGCGAAGCTGCTGGGTATG-3' (SEQ ID NO: 18)
ztsg1-MO: 5'-CTGATGATGATGATGAAGACCCCAT-3' (SEQ ID NO: 19)
zfz2MO-ATG:
  5'-CACACACACTTCCACTCGCCTGCAT-3' (SEQ ID NO: 20)
zfzMO-UTR: 5'-CCTGCATTGTCTCGAAAAGTTCCGC-3' (SEQ ID NO: 21)
Fli-1-UTR   MO:
  5'-CAATTTTCAGTGGAGCCCGACAATA-3' (SEQ ID NO: 22)
Fli-1-ATG   MO:
  5'-TAATAGTTCCGTCCATTTTCCGCAA-3' (SEQ ID NO: 23)
Fli-1.3 MO: 5'-TCCGTCCATTTTCCGCAATTTTCAG-3' (SEQ ID NO: 24)

Example 4

Injections of Polynucleotide Analogues

The analogues MOs, 2'O-methyl RNA, and 3'-5' phosphoroamidate were solubilized in water at a concentration of 8 mM (approximately 65 mg/ml). The resulting stock solution was diluted to working concentrations of 0.09 to 3.0 mg/ml in water or 1× Danieau solution (58 mM NaCl, 0.7 mM KCl, 0.4 mM $MgSO_4$, 0.6 mM Ca $(NO_3)_2$, 5 mM HEPES pH 7.6). Analogue solutions were injected into the yolk as described in Ekker et al. (1995) *Curr Biol* 5:944–955. Analogue injections were preformed using a method similar to that used for mRNA injections. Briefly, zebrafish eggs were collected and transferred onto agarose plates as described in Westerfield (1995) *The Zebrafish Book: A Guide for the Laboratory Use of Zebrafish* (*Brachydanio rerio*) $3^{rd}$ Edition, University of Oregon Press. While agarose plates for mRNA injections were kept cold to slow embryo development, the plates for analogue injections were prewarmed to approximately 20° C., since analogue injection into cold embryos were found to increase non-specific effects and mortality of the injected embryos.

Needles used for analogue injections were the same as for mRNA injections (Hyatt and Ekker (1999) *Methods in Cell Biology* 59:117–126). The needles were back-filled with a pipette and calibrated by injecting the loaded morpholino solution into a glass capillary tube. The picoinjector volume control was then setup for 1.5 to 15 nL. The injection volume depended on the required dose, usually 1.5 to 18 ng of analogue was injected. Analogue solutions were injected through the chorion into the yolk of zebrafish embryos. The injected embryos were transferred to petri dishes containing system water and allowed to develop at 28° C.

Injections of buffered Danieau-MO solutions resulted in lower mortality rates in injected embryos compared to injections of water-MO solutions. No difference in the penetrance of the observed phenotypes, however, was seen betweeen embryos injected with buffered Danieau or water solution. The injection volume was 1.5 nL to 15 nL for all analogues depending on the required injected dose. For wild type or heterozygous E-line embryos of 1 to 16 cell stages, analogues were injected into the yolk.

Embryos that received two different MOs were injected twice, one injection for each MO. In experiments involving injection of two different MOs, embryos injected with only a single MO were analyzed and compared with embryos injected with two different MOs.

Effective doses were determined separately for each analogue. For example, at the effective dose of 4.5 ng and lower for the GFP-MO, reduction of GFP protein was detected, and $\geq 90\%$ of the GFP-MO-injected embryos developed normally as assayed using standard morphological criteria. Higher doses of the GFP-MO resulted in a larger average reduction of GFP protein, but also caused some detectable detrimental effects on development. These higher doses were not pursued further for this MO. In all cases shown, the dose used for analysis resulted in embryos of two classes, those displaying a specific phenotype or those that were normal when assessed using morphological criteria. A small fraction of embryos (typically $\leq 5\%$) developed abnormally due to mechanical damage following microinjection. Penetrance number for a specific MO and concentration was assessed by examining morphology of injected embryos. A minimum sample size of 25 was used.

PNAs (chordin and nacre 25-mer PNAs) were diluted in water to a concentration of 0.25 mg/ml (resulting in a solution with final pH=5). The resulting solutions were incubated at 55° C. for 5 minutes and placed on ice. The PNA solutions were injected into the yolk of zebrafish embryo as described for morpholino phosphorodiamidate (MO), 2'O-methyl RNA, and other injections. In contrast to work with MOs, PNAs display a mosaic distribution if injected later than the 4-cell stage. Furthermore, precipitation of a significant fraction of the injected PNA at the site of injection was observed in the injection of PNA at doses of 1.5 ng per embryo or higher.

Example 5 mRNA Injections

Synthetic mRNA was injected, as described in Ekker et al. (1995) *Curr Biol* 5:944–955, into the yolk of zebrafish embryos previously injected with the indicated MO. Siblings from the same pool of MO-injected embryos served as internal controls for these experiments.

For *Xenopus*, mRNA microinjections were performed at the 4-cell stage using 0.3×MMR, 3.5% ficoll. Dorsal-ventral polarity of early cleavage stage embryos was determined using pigmentation differences (Cho et al. (1991) *Cell* 67:111–120).

Synthetic mRNAs were designed such that any overlap between the synthetic mRNA and the MO would be insufficient for MO targeting. The oep mRNA used did not contain any overlap with the oep-MO. The twhh mRNA used contained only a six base overlap with twhh-MO, a degree of overlap previously shown to be insufficient for MO targeting in vitro and in tissue culture studies (Summerton (1999) *Biochim Biophys Acta* 1489:141–158 and Summerton et al. (1997) *Antisense Nucleic Acid Drug Dev* 7:187–195). Chordin mRNA from *Xenopus* was used in order to avoid any sequence homology with the zebrafish chordin-MO, and because previous studies showed *Xenopus* and zebrafish chordin genes encoded equivalent specific activities in *Xenopus* embryos (Miller-Bertoglio et al. (1998) *Dev Biol* 214:72–86).

Example 6

FITC-dextran Injections, Tissue Sectioning, and Visualization

Microangiography was performed as described in Weinstein et al. (1995) *Nat Med* 1:1143–7. Fluorescein isothiocyanate-dextran (FITC-dextran) having a molecular weight of 2,000,000 Daltons (SIGMA, catalog #FD-2000S) was used for these studies. The dextran was solubilized in 1× Danieau solution at 2 mg/ml concentration. Approximately 10 μl of the prepared solution was injected into sinus venosa/cardinal vein of anesthetized 48-hour embryos.

Embryos injected with FITC-dextran were fixed overnight, embedded into paraffin using standard procedures, and sectioned. Histological haematoxylin-eosin staining of the sections was subsequently carried out using standard protocols.

Both FITC-dextran injected embryos and unprocessed tissue sections (i.e. unstained sections) were visualized using a ZEISS Axioskop 2 microscope with a standard FITC filter set.

Example 7

Digital Photography

Bright field and in situ photography were performed on a ZEISS Axioplan 2 microscope using Nikon CoolPix 990 (bright field) or Kodak DCS 420 (in situ) digital cameras. For fluorescent photography, a ZEISS AxioCam or a Nikon CoolPix 990 digital camera was used.

Example 8

Fluorescence Analysis

Embryos injected with FITC-labeled antisense polynucleotide analogues were analyzed using FITC filters on a Zeiss Axioplan2 fluorescence microscope. Images were obtained using a Kodak DCS420 Digital Camera.

Fluorescence pictures of groups of embryos were taken using a MICROIMAGE I30B Low Light Integrating Camera and captured using a DC30+ analogue to digital video capture board (Pinnacle Systems) at maximum resolution (640×480) settings. Signal intensities were set to sub-saturation levels for maximal information capture. Sub-saturation level of signal intensity was determined using uninjected E-line embryos. Fidelity of capture was confirmed by simultaneously imaging both analogue and digital video shots. The resulting images were imported into Adobe Photoshop 5.0 for quantitative analysis. The background for each image, established using the "Selective Color" algorithm, was set to the same setting in all images. The "Mean" value of the "Histogram" algorithm was used to measure the green channel signal; the other channels were removed to minimize non-specific background. All scores were normalized to the values obtained from uninjected E-line (100%) and wild type (0%) data points.

Example 9

Western, Northern, and in situ Hybridization Analyses

For detection of GFP or NTL protein, standard western analysis was performed using GFP antibody (Clontech) or NTL antibody (gift of S. Schulte-Merker). Proteins isolated from pools of injected embryos were used. The amount of protein analyzed per sample was equivalent to the amount of protein obtained from five embryos.

For antibody staining, rabbit anti-phospho Mad antibody, a gift from P. ten Dijke, was used at 1/2000 dilution. Staining was visualized using an alkaline phosphatase-coupled secondary antibody (Promega laboratories).

For detection of GFP mRNA, Northern blot hybridization was performed according to standard procedures. A 700 base pair fragment from a Pst I digest that corresponded to the GFP coding region was used as probe. Each sample analyzed consisted of 5 μg total RNA isolated from a pool of 30 embryos. Two independent analyses were performed.

For whole-mount in situ hybridization, methods described by Mason et al. (1994) *Genes and Development* 8:1489–1501 and Jowett (1999) *Methods in Cell Biol* 59:63–85 were used. Hybridization was performed at 65° C. T7 polymerase was used for riboprobe synthesis. Riboprobes for fli-1 and flk-1 were synthesized using plasmids zffli-1 and zfflk-1 (Thompson et al. (1998) *Dev Biol* 197:248–69) digested with EcoR I and Sma I, respectively.

Example 10

Uniform Distribution of Injected Modified Polynucleotide Analogues in Early Zebrafish Embryos The delivery efficiency of modified polynucleotide analogues was determined using FITC-labeled analogues. FITC-labeled modified polynucleotide analogues were injected into embryos at the 1-2-cell stage. Modified polynucleotide analogues that were injected included MOs, peptide nucleic acids (PNA), 2'-O methyl RNA, and 3'-5' phosphoroamidate. Distribution of FITC-labeled polynucleotide analogues was examined by fluorescence microscopy as described in Examples 7 and 8. Injected embryos were compared with uninjected control embryos. Results demonstrate that polynucleotide analogues were completely translocated to blastomeres as early as the 8-cell stage (less than 1 hour after injection). Polynucleotide analogues remained uniformly distributed among blastomeres as evident from samples at the mid-blastula stage.

In a second distribution study, 90 pg of FITC-labeled control-MO or FITC-labeled chordin-MO were injected into wild type zebrafish embryos from 1 to 16 cell stages of development. Uniform distribution of FITC-labeled-MOs was achieved at sphere and 28 hour stages. Injection of a chordin-MO dose of 90 pg resulted in embryos that developed normally.

In a third distribution study, FITC-labeled PNA-2 (Gene Therapy Systems) was microinjected into yolks of 1–16 cell zebrafish embryos. Injection volumes were 6 to 15 nl; approximately 50–200 ng was injected. Buffer from Gene Therapy Systems or 0.5× Danieau buffer was used. Toxicity was not observed with either buffer. From 85–90% of the injected embryos survived at 48 hours of development (usual survival rate for non-toxic injections). Older embryos were not analyzed. The fluorescence signal was detected in all tissues at comparative levels. The distribution was uniform as determined by fluorescence microscopy. Isolated points of high signal concentration, however, were observed (<10 per embryo, at approximately 1 cell diameter).

Example 11

Specific Inhibition of GFP Transgene Expression in all Cells of a Zebrafish Embryo by GFP-MO A non-essential ubiquitous GFP transgene was used to test the applicability of antisense MOs as a general gene knockdown strategy in zebrafish. A GFP-targeted MO (GFP-MO) was injected into zebrafish E-line embryos. Fluorescence and western blot assays were used to examine GFP transgene expression. GFP fluorescence of (1) uninjected E-line embryos, (2) E-line embryos injected with 4.5 ng of control-MO, (3) E-line embryos injected with 4.5 ng of GFP-MO, and (4) wild type embryos was compared by FITC illumination. GFP fluorescence in uninjected E-line embryos was ubiquitous. Similarly, GFP fluorescence in E-line embryos injected with 4.5 ng of a control-MO or a four base mismatch GFP-MO (GFPD4-MO) was near wild type. In contrast, GFP transgene expression was inhibited in all cells of the zebrafish E-line embryo injected with 4.5 ng of GFP-MO. The specific loss of GFP signal in embryos injected with GFP-MO was noted in nine separate experiments; at least 30 embryos were assayed in each experiment. The lack of visible GFP fluorescence indicated that a nearly complete loss of GFP protein expression was achieved. Furthermore, GFP-MO inhibition of GFP expression was dose-dependent. FIG. 1 is a GFP fluorescence inhibition graph demonstrating sequence-specific and dose-dependent inhibition of GFP expression. GFP activity in embryos injected with the control-MO and in embryos injected with the GFP-MO was compared. Fifteen embryos were assayed for each data point shown. Fluorescence activity data were confirmed by western blotting. These data demonstrate that specific inhibition of gene expression in all cells of the 28-hour zebrafish embryo was achieved using MOs.

Example 12

Inhibition of Chordin Expression by Chordin-MO

Figure 2:
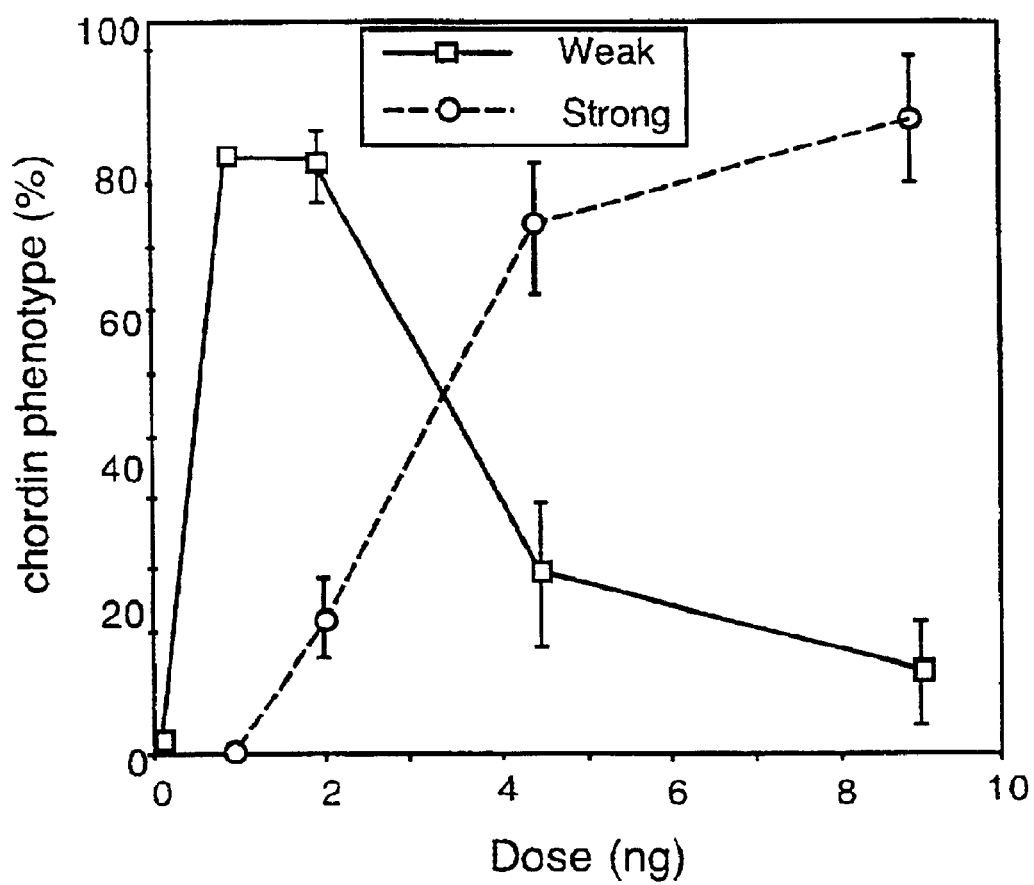
FIG. 2 is a graph demonstrating that two chordin-MO phenotypes, weak and strong, were achieved with increasing doses of chordin-MO injected.

A chordin antisense MO (chordin-MO) was injected into zebrafish embryos and a highly specific series of phenotypes dependent upon dose was observed in 28-hour embryos and 3-day old embryos. Embryos injected with various amounts of chordin-MO were compared with wild type embryos. The numbers of embryos injected with particular amounts of chordin-MO were as follows: 169 embryos were injected with 0.09 ng MO; 97 embryos were injected with 0.9 ng MO; 399 embryos were injected with 1.5 ng MO; 423 embryos were injected with 4.5 ng MO; and 224 embryos were injected with 9 ng MO. FIG. 2 is a graph demonstrating that two chordin-MO phenotypes, weak and strong, were achieved with increasing doses of chordin-MO injected. At low doses, a weak chordin-MO phenotype, the equivalent of a reduced chordin loss of function phenotype, was noted. Embryos displaying the weak chordin-MO phenotype had partially expanded blood islands, u-shaped somites, and abnormal tail fins with multiple folds. At higher doses, chordin-MO injected embryos exhibited a phenocopy of chordin null mutant embryos (Fisher et al. (1997) *Development* 124:1301–1311; Hammerschmidt et al. (1996) *Development* 123:95–102), i.e. the strong chordin-MO phenotype. This strong chordin-MO phenotype was observed at high frequency in high dose injections (≧75% at 4.5 ng MO injection, n=423), and consisted of abnormal u-shaped somites, extremely expanded blood islands, abnormal tail fins, and reduced heads. About 80% of the epiboly embryos subjected to in situ hybridization for otx-2 showed reduction of otx-2 consistent with head reduction. About 65% of epiboly embryos subjected to in situ hybridization for gata-2 showed that the gata-2 expression domain was greatly enlarged and shifted anteriorly, indicating ventralization of the mesoderm. (Gata-2 was expanded in 100% of the injected embryos; n=30). Comparison of injected embryos with uninjected embryos demonstrated posterior fusion of gata-2 expression stripes. These results demonstrate that the equivalent of an allelic series for the loss of the chordin gene was achieved by the use of different doses of the chordin-MO.

Figure 3:
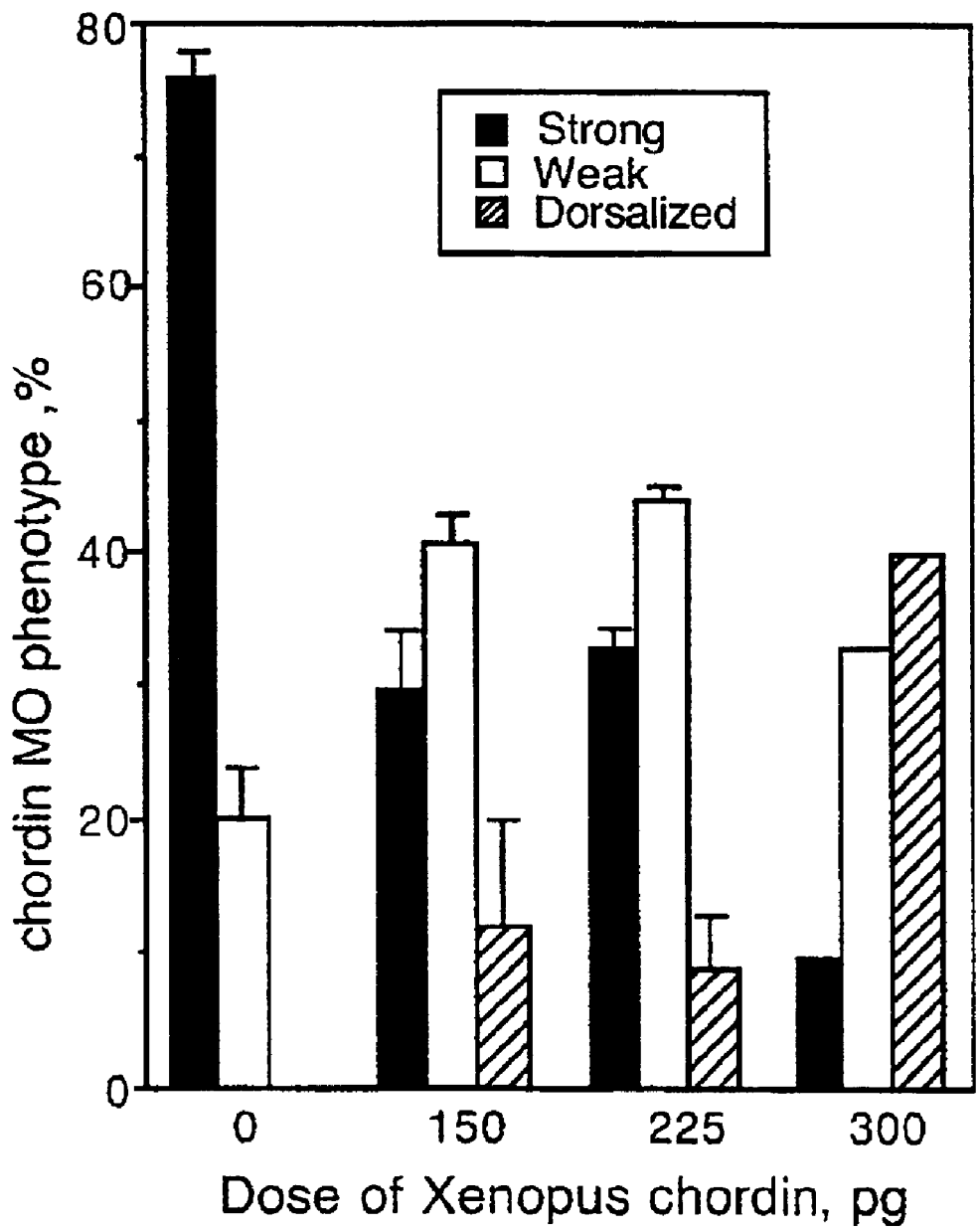
FIG. 3 is a bar graph demonstrating that the chordin-MO phenotype was partially rescued by *Xenopus* chordin mRNA injection, thereby illustrating specificity of chordin-MO targeting.

Whole-mount in situ hybridization for chordin mRNA was performed. Comparison of injected and uninjected embryos demonstrated that chordin mRNA levels were similar. Therefore, inhibition of chordin function by chordin-MO was not mediated by the conventional RNAseH mediated antisense-targeted degradation of chordin mRNA. To verify the specificity of gene targeting by chordin-MO, embryos were injected with synthetic *Xenopus* chordin mRNA to determine if effects of chordin-MO can be reversed. When 423 embryos were injected with 4.5 ng of chordin-MO, 76% showed the strong chordin phenotype. In contrast, when 30 embryos were injected with 4.5 ng of chordin-MO and 300 pg of *Xenopus* chordin mRNA, 10% exhibited the strong chordin phenotype. FIG. 3 is a graph demonstrating that the chordin-MO phenotype was partially rescued by *Xenopus* chordin mRNA injection, thereby illustrating specificity of chordin-MO targeting.

Example 13

Inhibition of Chordin Expression by Chordin-PNA

Twenty-five-base chordin-PNA (chd-PNA) and nacre-PNA were injected into zebrafish embryos as described in Example 4. Injected embryos were compared to wild type embryos. The resulting phenotypes were observed in 28-hour old embryos.

The numbers of embryos injected with particular amounts of chordin PNA were as follows: 41 embryos were injected with 0.25 ng chd-PNA; 130 embryos were injected with 0.5 ng chd-PNA; 98 embryos were injected with 1 ng chd-PNA; 77 embryos were injected with 1.5 ng chd-PNA. The numbers of embryos injected with particular amounts of nacre-PNA were as follows: 38 embryos were injected with 0.25 ng nacre-PNA, 71 embryos were injected with 0.5 ng nacre-PNA; 78 embryos were injected with 1 ng nacre-PNA; 75 embryos were injected with 1.5 ng nacre-PNA.

A weak ventralization, equivalent to the weak phenotype observed in chd-MO injection, was observed in 13% of the embryos injected with 0.25 ng of chd-PNA. Non-specific effects were noted in 6% of the injected embryos, while mortality rate was 22%. In the embryos injected with 0.5 ng chd-PNA, 31% mortality rate was observed. About 38% of the injected embryos exhibited a weak ventralization phenotype, while 2% exhibited a strong ventralization phenotype similar to a null chordin mutant phenotype. Non-specific effects were observed in 43% of the injected embryos. Injection with 1 ng and 1.5 ng of chd-PNA resulted in 74% and 76% mortality rates, respectively. The injection phenotypes were not analyzed.

Epiboly stage embryos were subjected to in situ hybridization to confirm morphological results. These analyses indicated that 28% of the chd-PNA injected embryos had expanded gata-2 expression, a hallmark of mesoderm ventralization. In situ hybridization for otx-2 showed that 50% of zebrafish embryos injected with 0.5 ng chd-PNA and 70% of zebrafish embryos injected with 1 ng and 1.5 ng chd-PNA had reduced otx-2 expression. Reduction of otx-2 expression is indicative of embryo ventralization by the chd-PNA.

Nacre-PNA injections resulted in low to moderate mortality rates. Injections of 0.25 ng, 0.5 ng, 1 ng, and 1.5 ng of nacre-PNA resulted in mortality rates of 12%, 24%, 36%, and 35%, respectively. Non-specific abnormality rates ranged from 3% for injections of 0.25 ng and 0.5 ng to 12% for injection of 1.5 ng of nacre-PNA. No ventralization phenotype was observed in embryos injected with nacre-PNA. Furthermore, analysis of 2 day-old zebrafish embryos showed that injection with nacre-PNA had no effect on the nacre gene activity. In situ hybridization analysis of injected embryos showed that nacre-PNA injection did not alter gata-2 or otx-2 expression. These results indicate that the ventralization phenotype is specific to chordin-PNA.

Example 14

Inhibition of Maternal Gene Expression by oep-MO

The one-eyed pinhead gene (oep) (Zhang et al. (1998) Cell 92:241–251) was selected to test for maternal gene activity inhibition by MO. Embryonic oep function is due to both maternal and zygotic genetic contributions that are distinguishable based on specific criteria (Gritsman et al. (1999) Cell 97:121–132). Embryos deficient in oep function are defective in signaling through the nodal pathway. Embryos were injected with 9 ng of oep-MO, and phenotypes consistent with loss of zygotic oep function were seen. Cyclopia and ventral curvature typical of zygotic oep mutants were observed in 30±5% of embryos (n=291). In 13±5% of embryos (n=291), severe cyclopia, somite absence in the trunk, misshapen tail somites, and reduced notochord typical of a maternal-zygotic oep mutant were observed. Tailbud stage embryos were subjected to in situ hybridization for pax-2 and axial. Prechordal mesoderm reduction was seen in 45% of injected embryos when compared to wild type embryos; 24 embryos were analyzed.

Figure 4:
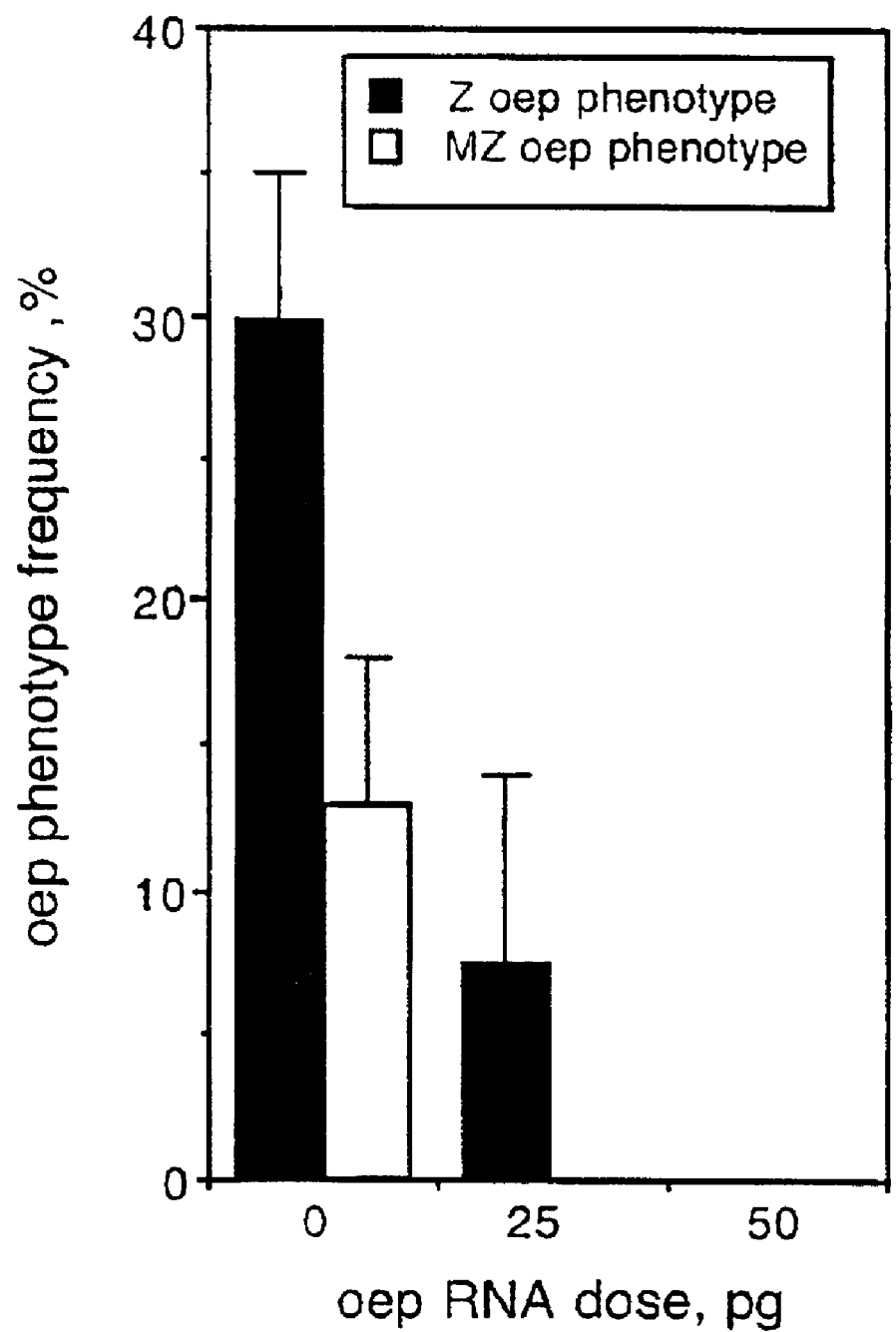
FIG. 4 is a bar graph demonstrating dose-dependent reduction in the frequency of the oep phenotype in response to oep mRNA injections.

The oep-MO phenotype was rescued by injection with synthetic zebrafish oep mRNA. Forty-three percent of embryos (n=291) displayed oep phenotypes when injected with 9 ng oep-MO, while none of the 33 embryos analyzed displayed oep phenotypes when injected with 9 ng oep-MO and 50 pg oep mRNA. FIG. 4 is a graph demonstrating dose-dependent reduction in the frequency of the oep phenotype in response to oep mRNA injections. This result demonstrates that the observed oep phenotype was due to the specific inhibition of oep gene function.

Injections with higher concentrations of oep-MO resulted in a phenocopy of the loss of both zygotic and maternal oep functions. MOs are thus capable of targeting maternal gene function, albeit at reduced levels compared to zygotic gene targeting.

Example 15

Use of Morpholinos to Identify Genetic Interactors

An MO targeted to the no tail (ntl) gene (Schulte-Merker et al. (1994) Development 120:1009–1015) was used to identify genetic interactors of ntl. Embryos (n=118) were injected with 9 ng of ntl-MO. Ninety-eight percent of the injected embryos were indistinguishable from those caused by a null mutation (Halpern et al. (1997) Dev Biol 187:154–170) when assessed using molecular and phenotypic criteria. Normal head, abnormal somites, and extremely reduced tail were prominent. When ntl-MO was injected into ntl mutant embryos (n=72), no additional defect was noted in the ntl mutant embryos due to the injection of ntl-MO. NTL protein was specifically and quantitatively reduced in wild type embryos injected with ntl-MO.

Activation of the somitic mesodermal marker myod requires input from both oep and ntl pathways (Schier et al. (1997) Development 124:327–342). When embryos were co-injected with 9 ng of ntl-MO and 9 ng of oep-MO, highly reduced head, reduced tail, and extremely reduced somites and notochord were observed. When 10–12 somite embryos were subjected to in situ hybridization for myod, embryos reduced in either ntl or oep function displayed an altered but robust expression of myod, while embryos reduced of both functions expressed myod in only a few cells. For example, 92% of ntl-MO injected embryo (n=25) exhibited adaxial mesoderm reduction and posterior somite fusion, and 41% of oep-MO injected embryos (n=22) exhibited posterior fusion of the adaxial mesoderm. In ntl-MO and oep-MO co-injected embryos (n=24), 52% exhibited no adaxial mesoderm and extremely reduced somitic mesoderm.

Figure 5:
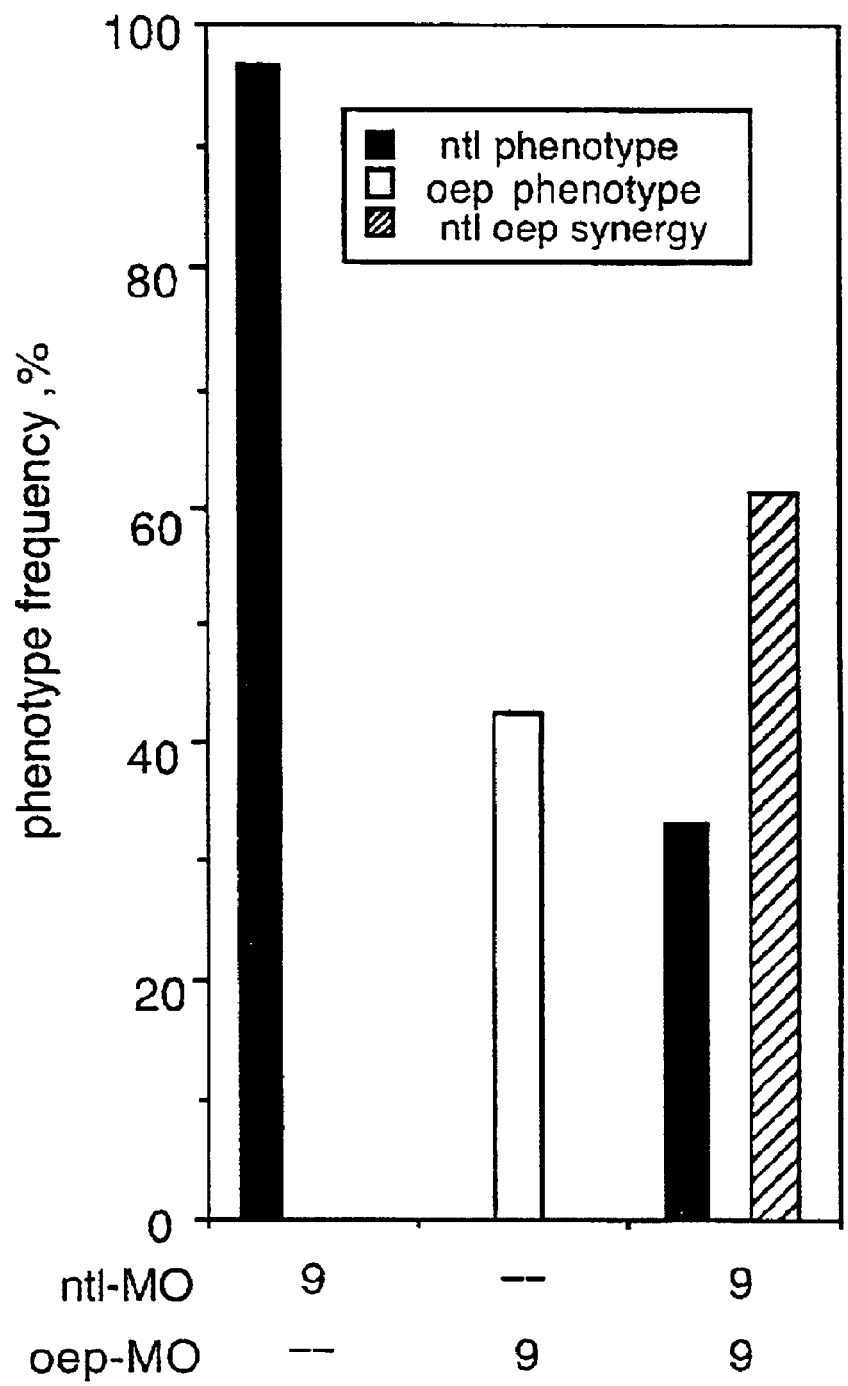
FIG. 5 is a bar graph comparing the frequencies of ntl, oep, and ntl and oep phenotypes observed in embryos injected with ntl-MO, oep-MO, or both MOs.

Whole-mount in situ hybridization of shh in 10–12 somite stage embryos demonstrated that 80% ntl-MO injected embryos (n=25) exhibited weak expansion of shh expression, while 50% of eop-MO injected embryos (n=22) exhibited strong expansion of the shh expression. Fifty-two percent of embryos co-injected with ntl- and oep-MO (n=31) exhibited severe reduction of shh expression. FIG. 5 is a graph comparing the frequencies of ntl, oep, and ntl and oep phenotypes observed in embryos injected with ntl-MO, oep-MO, or both MOs. MOs are thus effective tools for the testing of genetic interactions in vivo.

Example 16

Inhibition of Gene Expression Throughout Somitogenesis and Organogenesis

Later-acting genes were used to determine the perdurance of morpholino effects. One hundred and twelve embryos were injected with 9 ng of nacre-MO. Ninety-eight percent of injected embryos exhibited a characteristic and nearly complete loss of body pigmentation through the first 50 hours of development, a phenotype indistinguishable from that observed in the nacre mutant (Lister et al. (1999) Development 126:3757–3767). At later time points, pigmentation returned at a variable rate. One hundred and fifty-nine embryos were injected with 9 ng of sparse-MO. Injection of sparse-MO duplicated a known zebrafish pigment mutation sparse (Parichy et al. (1999) Development 126:3425–3436). When 65-hour and 10-day old zebrafish embryos were examined, 95% exhibited reduced numbers of pigmented cells (melanocytes). Dorsal melanocytes were significantly reduced in these embryos. Therefore, MO-based gene targeting was completely penetrant throughout the first two days, and potentially the first 10 days, of development. Furthermore, MO-based gene targeting was completely penetrant throughout the critical vertebrate processes of somatogenesis and organogenesis in the zebrafish embryo.

Example 17

Development of Morpholino-based Model Systems for Human Diseases

Hepatoerythropoietic porphyria (HEP) is caused by a defect in haem biosynthesis through loss of the uroporphyrinogen decarboxylase (urod) enzyme (Kappas et al. (1995) *The Metabolic Basis of Inherited Diseases*, pages 2103–2159). The manifestation of this syndrome includes fluorescent and photosensitive red blood cells. One hundred and eithteen embryos were injected with urod-MO, and then examined using a rhodamine filter set. Control-MO injected embryos were compared with urod-MO injected embryos. All of the injected embryos displayed both fluorescent and photosensitive red blood cells as had been noted in a hypomorphic urod mutation (Wang et al. (1998) *Nature Genet* 20:239–243). Intense auto-fluorescence in the injected embryos indicated accumulation of photosensitive porphyrins in the circulating blood cells. Photosensitivity of blood cells in urod-MO injected embryos was evident when embryos were exposed to light. Exposure to light resulted in depletion of all red blood cells in urod-MO injected embryos. The complete phenotypic penetrance of embryos injected with urod-MO demonstrates that a MO-based animal model of human disease was generated Holoprosencephaly (HPE) occurs at high frequency in human embryos (1:250) and in live births (1:16,000) (Wallis et al. (1999) *Mol Genet Metab* 68:126–138). In extreme cases, the phenotype is cyclopia. The gene sonic hedgehog (shh) is thought to play a critical role in the development of this disease in humans (Belloni et al. (1996) *Nature Genet* 14:353–356; Roessler et al. (1996) *Nature Genet* 14:357–360). Zebrafish shh mutations, however, result in no anterior midline signaling defects (Schauerte et al. (1998) *Development* 125:2983–2993). A second shh orthologue expressed in the anterior midline, tiggy-winkle hedgehog (twhh) (Ekker et al. (1995) *Curr Biol* 5:944–955), could explain this lack of phenotype in a highly conserved vertebrate developmental process. Both shh and twhh genes were targeted using MOs to test for redundancy and to develop zebrafish as a genetic model for HPE.

Figure 6:
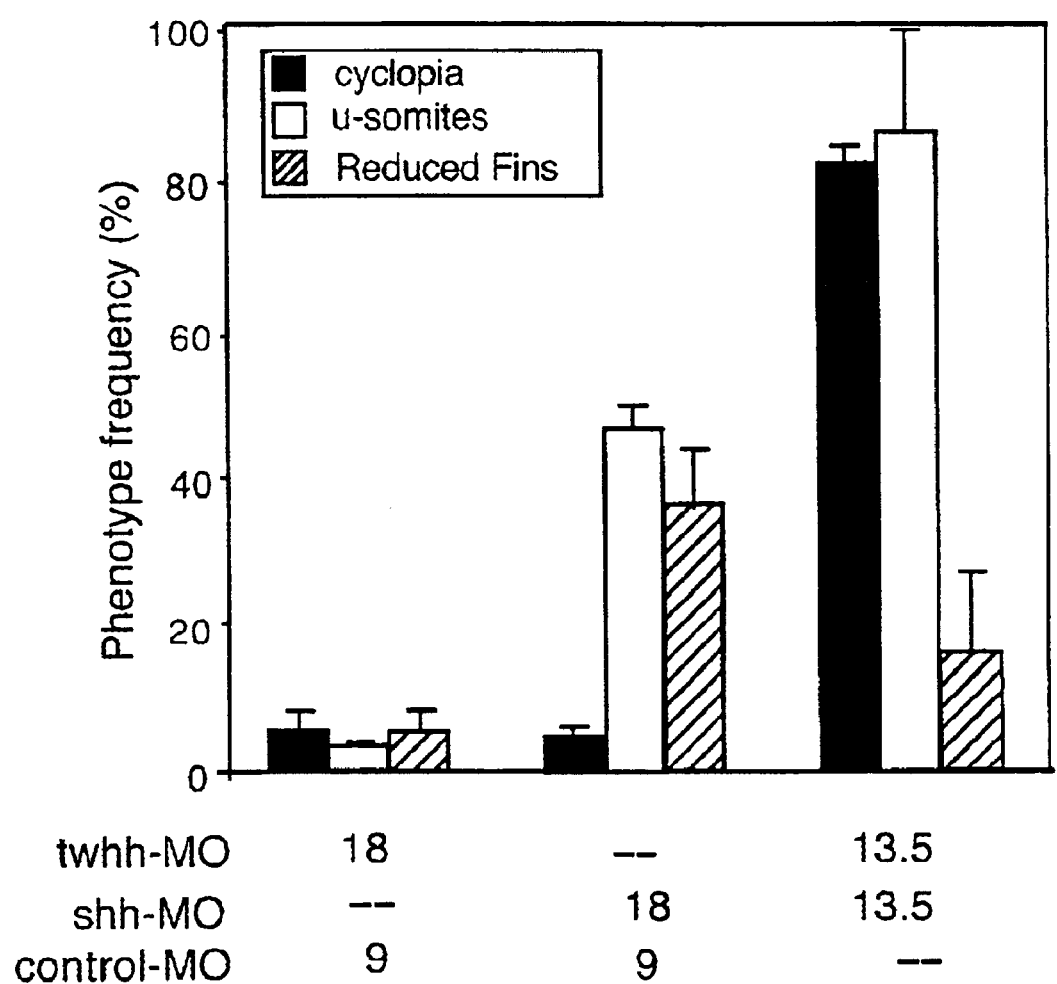
FIG. 6 is a bar graph comparing the frequencies of cyclopia, u-somites, and reduced fins in embryos injected with a control-MO and twhh-MO, a control-MO and shh-MO, or both twhh- and shh-MOs.

Embryos were (1) injected with 18 ng twhh-MO and 9 ng of control-MO; (2) injected with 18 ng shh-MO and 9 ng of control-MO; (3) co-injected with shh-MO and twhh-MO, 13.5 ng each; or (4) injected with shh-MO and twhh-MO (13.5 ng each), and 100 pg of twhh mRNA. Embryos at 3-day old or 10 somite stage were analyzed. FIG. 6 is a graph comparing the frequencies of cyclopia, u-somites, and reduced fins in embryos injected with a control-MO and twhh-MO, a control-MO and shh-MO, or both twhh- and shh-MOs.

Embyros injected with shh-MO exhibited phenotypes characteristic of a shh mutation (Schauerte et al. (1998) *Development* 125:2983–2993). These embryos displayed 'u'-shaped somites, lacked the horizontal myoseptum, and had reduced pectoral fins. Embryos injected with twhh-MO exhibited phenotypes indistinguishable from controls. These embyros had normal heads, 'v' shaped somites, and normal myoseptum when compared to wildtype embryos. Injection of both twhh-MO and shh-MO, however, resulted in embryos with synergistic defects in somitic patterning in the trunk, a new phenotype in the forebrain, partial cyclopia, absence of myoseptum, and loss of transcription of the hedgehog target gene patched (ptc) (Concordet et al. (1996) *Development* 122:2835–2846).

When 9 ng twhh-MO was injected into shh deficient embryos (n=52), 100% penetrance of partial cyclopia was achieved. In contrast, twhh-MO failed to cause any cyclopia in sibling embryos (0%, n=120) (S. Bingham and A. Chandrasekhar, in press). This suggests that zebrafish embryos contain two functionally redundant orthologues of the mammalian shh gene with similar roles in anterior midline patterning.

Embryos at the 10 somite stage were examined by wholemount in situ hybridization for myod. Results demonstrated that shh-MO injected embryos exhibited a weak reduction of adaxial and somatic mesoderm when compared to wildtype embryos. Embryos co-injected with shh-MO and twhh-MO exhibited an extreme reduction of adaxial mesoderm. This reduction was reversed and adaxial mesoderm was lightly expanded by injection of zebrafish twhh mRNA.

These results demonstrate that zebrafish is an effective model for HPE. In addition, these experiments demonstrate the utility of morpholinos for both single and multiple gene knockdowns for the understanding of vertebrate embryonic development and disease.

Example 18

Sonic Hedgehog MO Synergy

Figure 7A:
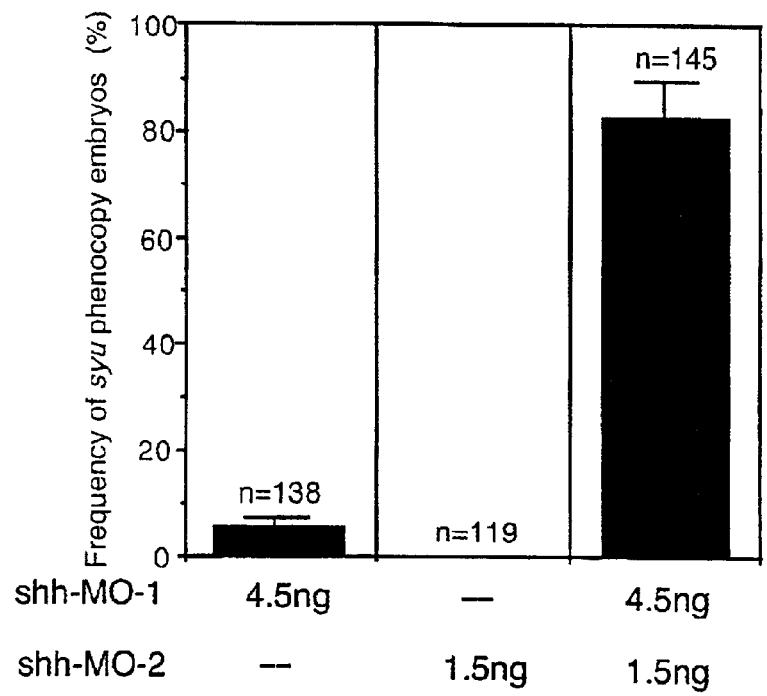
FIGS. 7A and 7B are bar graphs demonstrating synergy between two shh-MOs.
Figure 7B:
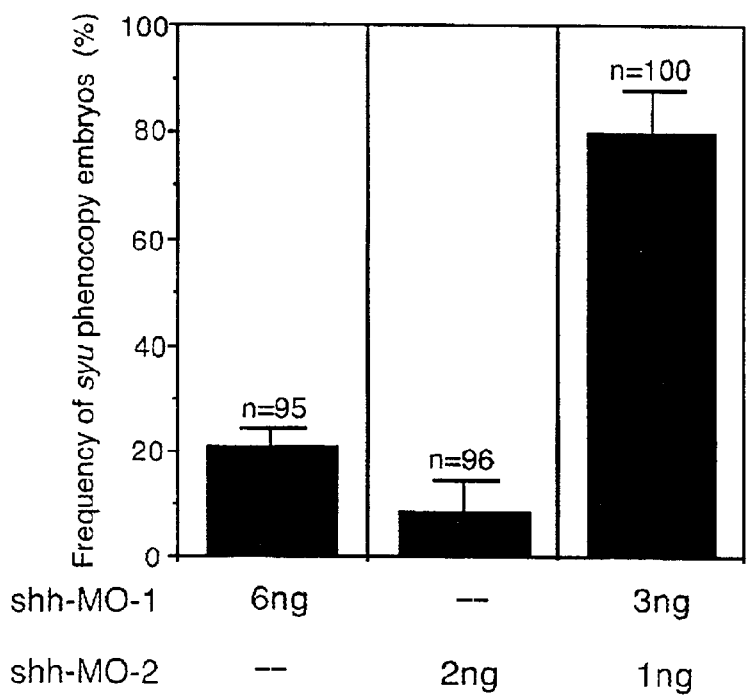

Embryos were injected, as described in Example 4, with two non-overlapping shh-MOs: shh-MO #1 and shh-MO #2. Sequences of shh-MO #1 and shh-MO #2 are provided in Example 3. Embryos were analyzed at 3 days of development for phenotypic changes resulting from loss of sonic hedgehog function (Schauerte et al. (1998) *Development* 125: 2983–2993). Embryos that displayed effects in somites as strong as the weakest allele tq252 were scored as demonstrating a positive phenotype. FIG. 7 compares the frequencies of embryos that displayed a phenotype associated with sonic hedgehog loss-of-function when injected with one or two shh-MOs. Results shown were obtained from three independent experiments. Twenty or more embryos were scored for each data point. As shown in FIG. 7A, the number of embryos having a sonic hedgehog loss-of-function phenotype resulting from morpholino injection was greater when embryos were injected with two shh-MOs than when embryos were injected with a single shh-MO. A comparison of the numbers of embryos having the sonic hedgehog loss-of-function phenotype resulting from injection of one or two shh-MOs demonstrates that the increase was more than additive, i.e., injection with two shh-MOs had a synergistic effect on the number of embryos exhibiting sonic hedgehog loss-of-function phenotype. Furthermore, injection of a half dose of two shh-MOs is much more potent at knocking down shh gene expression than a full dose of either MO alone (see FIG. 7B).

Example 19

Efficiency of Gene Inactivation by Morpholinos

Morpholinos were generated against known genes to determine an estimate of success rate. Genes targeted included shh, chordin, no tail, one-eyed-pinhead (oep), sparse, nacre, urod, bozozok/dharma, an EF1a-GFP transgene, pax 2.1, bmp1, bmp2b, bmp7, alk8, smad5, wnt5, and wnt11 (see Ekker (2000) *Yeast* 17:302–306). With the exception of pax 2.1, all genes targeted resulted in clear specific gene inactivation with the first MO tried, i.e., 16/17 or >94% of known genes were inactivated successfully. This rate of successful gene inactivation can be reduced by MO mistargeting or other non-specific effects. For example, an MO can inhibit a second gene resulting in embryos with a combined phenotype. An extreme example is represented by the bozozok/dharma MO, in which a second effect (CNS degeneration) is superimposed on the bozozok loss of function phenotype (Nasevicius et al. (2000) *Nature Genetics* 26:216–220). If these secondary, non-specific effects result in loss of embryonic structures or premature death of the embryo, then the function of the gene under study will not be scorable. The reduction in the rate of successful MO gene inactivation (16/17) by the rate of gene mistargeting (2/17) is a lower estimate of MO screening efficiency, and yields an initial MO screening rate of 82% (14/17). A significant fraction of these 'missed' genes can be recovered by the use of a second MO of unrelated sequence. Assuming a similar success rate of approximately 80% for the remaining 18% of 'missed' genes, an additional 14% of genes can be targeted by the second MO, for a combined expected success rate of >95% for genes screened using two targeted MOs.

Should the leader sequence in a specific locus be especially prone to polymorphism, the selected gene might not be inactivated in all embryos due to the high specificity of MO targeting in vivo. The one-eyed-pinhead locus is a potential example of this phenomenon (see Example 14); in one wild-type strain, only ~50% of embryos responded to this MO, in another, none. Other, less direct strain differences also could reduce the effectiveness of MOs. For example, variations in genetic backgrounds could alter the penetrance of a given MO effect due to genetic factors in a second, modulator locus. The characterization and inclusion of common 'wild-type' and other non-isogenic laboratory strains in the sequencing project is suggested to make maximum use of MO technology in zebrafish.

As with many genetic screens, MOs also are limited by functional redundancy, an issue especially relevant to vertebrates. Moreover, the zebrafish genome contains an additional set of incomplete duplicates for an estimated 30% of genes found in mammals (Postlethwait et al. (1999) *Methods Cell Biol* 60:149–163; and Oates et al. (1999) *Dev Dyn* 215:352–370). This partial genome duplication occasionally results in two orthologues in zebrafish for one in humans. One example is the sonic hedgehog locus (Example 17). Comparative expression profiles of likely orthologues, however, demonstrate only a duplication of a subset of expression patterns for these genes. Indeed, no two orthologues have identical expression patterns in zebrafish (Gates et al. (1999) *Genome Res* 9:334–347). The use of MOs, however, is highly amenable to rapid tests of redundancy through the simultaneous targeting of genes of related sequence (see Example 17). Multi-gene targeting strategies are thus practical using current morphino technology, with an estimated minimum success rate of (0.82×0.82)=67%. For genes amenable to this strategy, morpholinos will be extremely effective at identifying and testing molecules with redundant functions in vivo.

Example 20

Morphological Effects of VEGF-A-1 Morpholino Injection at 36 Hours

Signaling by members of the Vascular Endothelial Growth Factor (VEGF) gene family is implicated in the formation of vasculature during embryogenesis, during wound healing, and for the growth of tumor-induced vasculature (See Carmeliet et al. (1996) *Nature* 380:435–9; Carmeliet et al. (1997) *Am J Physiol* 273:H2091-104; and Ferrara (1999) *J Mol Med* 77:527–43). Pioneering work in mice with VEGF-A demonstrates the extreme dose responsiveness of the mouse embryo to VEGF-A signaling during development. Loss of a single copy of the VEGF-A gene induces haploinsufficient lethality by day 9.5 pc (Ferrara et al (1996) *Nature* 380:439–42); Carmeliet et al. (1996) *Nature* 380:435–9). This biological hurdle to the genetic investigation of VEGF-A requirements during later development has resulted in a series of experiments using conditional knockout strategies (Gerber et al. (1999) *Development* 126:1149–59; Haigh et al. (2000) *Development* 127:1445–53) or dominant negative proteins (Gerber et al. (1999) *Development* 126:1149–59). A more recent approach to address this problem used intravenous injection of anti-sense oligonucleotides in pregnant mice to reveal loss of function requirements of VEGF-A function during murine embryogenesis (Driver et al. (1999) *Nat Biotechnol* 17:1184–7).

Zebrafish embryos develop externally and have only limited requirements for a functioning circulatory system during early development. For example, embryos with no circulating red blood cells due to porphyria live through the first three days of development (Ransom et al. (1996) *Development* 123:311–9), a period that includes all of segmentation and organogenesis in the fish embryo. Multiple mutations in cardiovascular development were isolated in the initial large-scale chemical mutagenesis screens (Stainier et al. (1996) *Development* 123:285–92; Chen et al. (1996) *Development* 123:293–302; Weinstein et al. (1995) *Nat Med* 1:1143–7). Together, the zebrafish has the potential to rapidly assess the biological role of angiogenic factors required for this essential vertebrate process.

Zebrafish VEGF-A is expressed during embryogenesis in the anterior nervous system, in mesoderm flanking the prospective heart fields, and in somitic mesoderm that flanks the developing endoderm (Liang et al. (1998) *Biochim Biophys* 1397:14–20). MOs were generated against VEGF-A to analyze the requirement of this gene during embryonic development. MOs had been shown to be effective at gene inactivation during the first two days of zebrafish development (see Example 16).

Embryos were injected with 9 ng of VEGF-A-1-MO. The resulting VEGF-A morphant embryos developed with no overt abnormal phenotype during the first day of development. At two days of embryogenesis, the VEGF-A morphant phenotype consisted of an enlarged pericardium, no circulating red blood cells, a slight reduction in neural tube and overall body size, and little or no functioning vasculature. In a subset of embryos, red blood cell accumulation was observed in the ventral tail. Table 1 summarizes the frequencies of embryos exhibiting loss of vasculature, pericardial edema, blood accumulation in the anterior aorta, and blood accumulation in the tail when injected with the indicated amounts of MO.

Four experiments were performed at each MO dose. Average frequencies of all experiments performed at each MO dose are shown. The standard error is the mean of the differences between the average frequency and the frequencies of individual experiments.

TABLE 1

Microangiography analysis of embryos injected with VEGF-A-1-MO at 48 hours.

| Observed phenotypes (frequency, %) | Injected VEGF-A-1 morpholino dose, ng | | | | |
|---|---|---|---|---|---|
| | 3 | 6 | 9 | 12 | 18 |
| Heart and yolk vasculature only | 3 ± 2 | 3 ± 1 | 21 ± 4 | 38 ± 13 | 39 ± 1 |
| No axial or intersegmental vasculature | 7 ± 4 | 2 ± 1 | 25 ± 3 | 27 ± 13 | 29 ± 9 |
| No/reduced intersegmental vasculature | 67 ± 5 | 78 ± 13 | 51 ± 2 | 36 ± 20 | 30 ± 6 |
| Normal vasculature | 23 ± 10 | 17 ± 16 | 3 ± 1 | 0 ± 0 | 2 ± 3 |
| Pericardial edema | 15 ± 2 | 35 ± 10 | 49 ± 2 | 55 ± 0 | 57 ± 2 |
| Blood accumulation in anterior hypochord | 0 ± 0 | 1 ± 1 | 5 ± 3 | 3 ± 0 | 8 ± 2 |
| Blood accumulation in tail | 1 ± 1 | 2 ± 2 | 16 ± 8 | 19 ± 0 | 19 ± 7 |
| Total embryo number | 110 | 120 | 105 | 106 | 101 |

Example 21

Microangiography Visualization of Vasculature Defects in VEGF-A-1 Morphants

Two separate fluorescent assays were used to assess vascular function. In the first assay, fluorescently-labeled RBCs were generated through inactivation of the uroporphyrinogen decarboxylase gene (urod; Wang et al. (1998) Nature Genet 20:239–243) using 9 ng of urod-MO. In 36-hour embryos injected with 9 ng of urod MO, fluorescing RBCs highlighted the axial vasculature, head vasculature, yolk sac, and heart. In embryos injected with 9 ng of VEGF-A-1-MO, RBCs were localized only to anterior aorta.

In the second assay, the vasculature was directly analyzed by injection with FITC-dextran. Injection of FITC-dextran into the sinus venosa/cardinal vein of an anesthetized 48-hour old embryo results in labeling of the entire vasculature of the zebrafish embryo, including the yolk sac, heart, head, axial, and intersegmental blood vessels (Weinstein et al. (1995) Nat Med 1:1143–7).

Injection with VEGF-A-1-MO showed that these structures were differentially sensitive to VEGF-A signaling. Further, three phenotypic classes were observed when various amounts of VEGF-A-1-MO were injected. In the most severe phenotypic class, i.e., at high dose injections of VEGF-A-1-MO, the only vasculature detectable was in the heart and yolk. Head, axial, and intersegmental blood vessels were not visible. The vasculature either failed to form at all or contained no functioning connections to the heart in these embryos. To distinguish between these possibilities histological analyses were performed on the most severely affected embryos. Neither dorsal aorta nor axial vein could be seen in the injected embryos.

A frequent but less severe phenotypic class of embryos also was observed. These embryos were said to exhibit a moderate VEGF-A-1-MO injection effect. In these embryos, the injected FITC-dextran highlighted yolk sac, heart, and head blood vessels only. No axial or intersegmental vasculature was observed.

The least severe phenotypic classification included embryos exhibiting reduced intersegmental vasculature, but normal heart, yolk, head, and axial blood vessels. Embryos exhibiting no or few intersegmental blood vessels, but normal yolk sac, heart, head vasculature, and axial blood vessels were said to exhibit a weak VEGF-A-1-MO effect.

The penetrance of these phenotypic classes was dependent on dose (see Table 1). This is consistent with the strong dose-dependence of VEGF-A function in mouse embryos (Ferrara et al. (1996) Nature 380:439–42; Carmeliet et al. (1996) Nature 380:435–9). Heterozygous mouse VEGF-A mutants showed a reduced dorsal aorta detected by histological analysis. Fewer intersegmental blood vessels were detected by a tissue-specific lacZ expression. Lack of dorsal aorta was indicated by histological analysis in homozygous mouse VEGF-A mutants (Carmeliet et al. (1996) Nature 380:435–9), suggesting that the most severe zebrafish VEGF-A morphant class represents a nearly complete loss of function phenotype. Although mouse VEGF-A mutants also displayed heart with under-developed myoblast (Ferrara et al. (1996) Nature 380:439–42; Haigh et al. (2000) Development 127:1445–53), the heart in zebrafish VEGF-A morphants had essentially a normal appearance with a slightly enlarged atrium and ventricle, possibly due to higher cardiac pressure.

Example 22

Confirmation of VEGF-A MO Specificity

Two VEGF-A-MOs, one having a sequence that did not overlap with VEGF-A-1-MO and one containing a four base mismatch, were used to confirm specificity of targeting (see Table 2). Four VEGF-A-D4-MO injection experiments and two VEGF-A-3-MO injection experiments were performed at each MO dose. Table 2 summarizes the average frequencies observed in all experiments performed at each MO dose. The standard error is the mean of the differences between the average frequency and the frequencies of individual experiments.

Injection of embryos with VEGF-A-D4, the mismatched-MO, demonstrated the sequence-specific nature of the noted effects of the VEGF-A-1-MO (see Table 2). To independently test for specificity of targeting to the endogenous VEGF-A gene, a second VEGF-A-MO of completely independent sequence (VEGF-A-3) was used. This very potent MO caused the same phenotypic effects on development as the VEGF-A-1-MO, including a dose-dependent reduction of vascular function, pericardial edema, and blood accumulation in the tail (see Table 2). The differential efficacy might be due to different secondary structures of the MOs or the targeted mRNA regions. Alternatively, the effect might be caused by the higher predicted melting temperature of VEGF-A-3 (48% G/C) compared to VEGF-A-1 (28% G/C). Therefore, phenotypes associated with injection of VEGF-A-1-MO resulted from MO-based specific inhibition of translation of VEGF-A transcripts.

A number of genes whose mutation results in cardiovascular defects have been observed in chemical mutagenesis screens with zebrafish (Stainier et al. (1996) *Development* 123:285–92; Chen et al. (1996) *Development* 123:293–302). Although none of the phenotypes associated with these mutations strongly resemble the VEGF-A morphant phenotype, the mutant embryos had overlapping phenotypes. Mutations in multiple loci result in embryos with cardiac edema, and a similar accumulation of blood in the ventral tail fin was noted due to disorganized endothelia in the scotch tape (sco) mutation (Chen et al. (1996) *Development* 123:293–302). Several mutations giving rise to altered circulation were noted (Stainier et al. (1996) *Development* 123:285–92); Chen et al. (1996) *Development* 123:293–302). These mutations included gridlock, a gene that encodes a bHLH protein required only for arterial development (Weinstein et al. (1995) *Nat Med* 1:1143–7; Stainier et al. (1996) *Development* 123:285–92); Zhong et al. (2000) *Science* 287:1820–4). The role of these genes in VEGF signaling awaits molecular genetic characterization of the remaining loci.

Similar results were obtained upon analysis of expression of the tyrosine kinase VEGF receptor flk-1. Distribution of flk-1 transcripts was very similar to that of fli-1 in the trunk and tail of wild-type embryos. In VEGF-A morphant embryos generated by injection with 9 ng VEGF-A-1, intersegmental but not axial expression was absent. A significant reduction in flk-1 gene expression was noted in mouse embryos with no VEGF-A activity (Carmeliet et al. (1996) *Nature* 380:435–9). A less extreme lack of flk-1 expressing cells in the intersegmental vasculature also was observed in mouse with the partial and conditional VEGF-A knockout (Haigh et al. (2000) *Development* 127:1445–53).

Zebrafish embryos injected with 18 ng of VEGF-A-1-MO displayed the same specific loss of expression only in the intersegmental regions for both fli-1 and flk-1. The lack of a requirement for VEGF signaling for flk-1 expression is consistent with previous observations of paracrine modes of VEGF signaling (reviewed in Ferrara, 1999). The expression of the VEGF receptor flk-1 is, however, VEGF-dependent

TABLE 2

Microangiography analysis of embryos injected with VEGF-A-D4 and VEGF-A-3-MO at 48 hours

| | Injected dose, ng | | | | |
|---|---|---|---|---|---|
| VEGF-A-D4 morpholino | 3 | 6 | 9 | 12 | 18 |
| Heart and yolk vasculature only | 1 ± 1 | 0 ± 0 | 2 ± 3 | 3 ± 0 | 3 ± 0 |
| No axial or intersegmental vasculature | 0 ± 0 | 0 ± 0 | 0 ± 0 | 0 ± 0 | 0 ± 0 |
| No/reduced intersegmental vasculature | 7 ± 0 | 6 ± 3 | 5 ± 2 | 22 ± 1 | 14 ± 3 |
| Normal vasculature | 92 ± 1 | 94 ± 3 | 93 ± 3 | 75 ± 2 | 84 ± 3 |
| Total embryo number | 163 | 116 | 119 | 76 | 73 |
| VEGF-A-3 morpholino | 0.5 | 1.5 | 3 | | |
| Heart and yolk vasculature only | 0 ± 0 | 13 ± 13 | 27 ± 11 | | |
| No axial or intersegmental vasculature | 0 ± 0 | 24 ± 24 | 40 ± 13 | | |
| No/reduced intersegmental vasculature | 18.8 | 37 ± 11 | 24 ± 14 | | |
| Normal vasculature | 81.2 | 26 ± 26 | 10 ± 10 | | |
| Total embryo number | 32 | 71 | 69 | | |

Example 23

Comparative Expression of fli-1 and flk-1 in 26 Hour-wild Type and VEGF-A-1 Morpholino Injected Zebrafish Embryos Expressions of two endodermal vascular markers, fli-1 and flk-1, in VEGF-A morphant embryos were analyzed. The transcription factor fli-1 is a very early marker of vascular cell fate specification (Thompson et al. (1998) *Dev Biol* 197:248–69; Brown et al. (2000) *Mech Dev* 92:237–52). In wild-type 26-hour embryos, fli-1 was expressed in the forming dorsal aorta and axial vein and in the intersegmental vasculature in overlying somites. In embryos that failed to complete vascular development, only a subset of the vascular expression patterns of fli-1 was altered. No detectable intersegmental expression of fli-1 was observed. This coincided with the exquisite intersegmental vascular endoderm sensitivity to VEGF signaling (Table 1). The cells either were not properly specified or failed to migrate during formation of the intersegmental vessels. The distinct responsiveness of the expression of the endothelial marker fli-1 in intersegmental vessels to VEGF-A signaling demonstrates a dual role for VEGF during vascular development. First, VEGF-A is required for proper axial vessel formation but not for initial axial vessel patterning. Second, VEGF-A is required for intersegmental vessel cell specification or migration, and presumably, for subsequent vascular formation.

during intersegmental vascularization. This latter observation suggests a possible autoregulatory loop, functioning during vasculogenesis of the intersegmental vessels. The strong conservation of VEGF function from fish to mammals implicates this as a fundamental vertebrate biological pathway.

These experiments demonstrate a fundamental distinction between VEGF-A requirements for axial and intersegmental vascular structure specification. More specifically, VEGF-A is not required for the initial establishment of axial vasculature patterning, whereas all development of intersegmental vasculature is dependent on VEGF-A signaling. The absence of axial and intersegmental vasculature in VEGF-A morphant embryos indicates that VEGF-A has a role beyond establishing flk-1 and fli-1 expression in blood vessel formation.

Example 24

VEGF-MO Synergy

Figure 8:
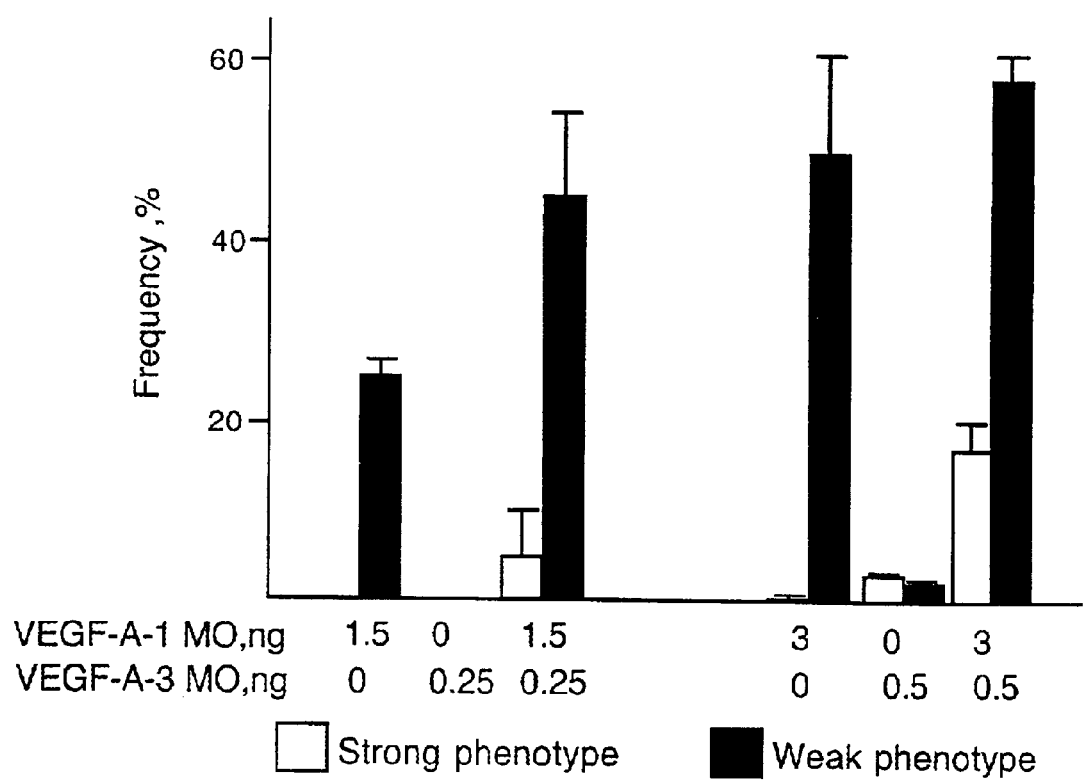
FIG. 8 is a bar graph demonstrating synergy between two VEGF-MOs.

Embryos were injected, as described in Example 4, with two VEGF-MOs: VEGF-A-1-MO and VEGF-A-3-MO. Sequences for the VEGF-A-1-MO and VEGF-A-3-MO are provided in Example 3. Embryos at 2 days of development were analyzed using microangiography, as described in Example 21. Embryos that displayed defects in intersegmental vasculature only were scored as displaying a weak VEGF-MO phenotype, whereas embryos that displayed defects in both intersegmental and axial vasculature were scored as a strong VEGF-MO phenotype. Results, depicted in FIG. 8, demonstrate that the number of embryos having a weak or strong VEGF-MO phenotype resulting from morpholino injection was greater when embryos were injected with two VEGF-MOs than when embryos were injected with a single VEGF-MO. A comparison of the numbers of embryos having the weak or strong VEGF-MO phenotype resulting from injection of one or two VEGF-MOs demonstrates that the increase was more than additive, i.e., injection with two MOs had a synergistic effect on the numbers of embryos exhibiting weak or strong VEGF-MO phenotypes.

Example 25

Zebrafish Frizzled-2 Targeting Analyses

Figure 9:
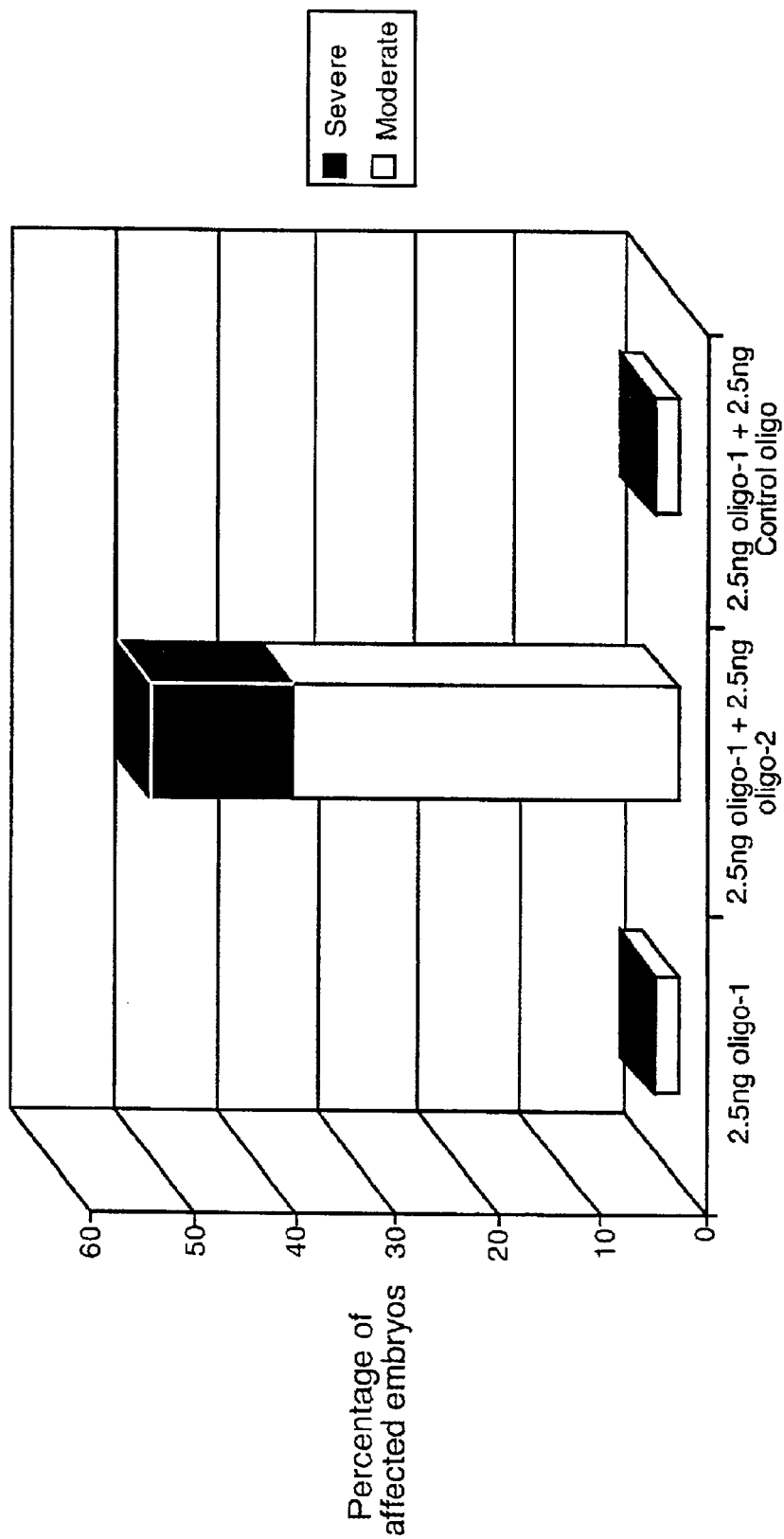
FIG. 9 is a bar graph demonstrating synergy between two zfz-MOs.

Embryos were injected, as described in Example 4, with two zfz2-MOs: zfz2-MO-ATG and zfz2-MO-UTR. Sequences for zfz2-MO-ATG and zfz2-MO-UTR are provided in Example 3. FIG. 9 is a bar graph showing the percentages of embryos affected by injection with either one of the two zfz2-MOs or both zfz2-MOs. The zfz2-associated developmental defects are undulating notochords and wider than normal posterior-concentrated somites during embryosgenesis. Embryos injected with either a single zfz2-MO or two zfz2-MOs were examined for these morphologically-visible defects. Both zfz2-MOs were capable of eliciting similar undulated notochord and somite defects when injected individually into an embryo. When both of the zfz2-MOs were injected into the same embryo, defects in notochord and somite developments were synergistic.

In addition, development of the zebrafish pancreas was examined using pancreas-specific markers such as Fspondin and islet-1. Fspondin and islet-1 are expressed by a subset of cells in the zebrafish pancreas, and the absence of expression of Fspondin or islet-1 indicates that pancreas development is defective. When Fspondin and islet-1 expressions were examined, reduced expression or a complete lack of expression was found in morpholino-injected embryos.

Example 26

Vertebrate Tsg Functions to Augment Chordin Inhibitory Activity

To examine the function of tsg in vertebrates, the function of the ztsg1 gene in zebrafish was analyzed using a ztsg 1-MO. The ztsg1 gene is the appropriate counterpart to the early embryonic Drosophila tsg since ztsg1 is expressed ubiquitously in early zebrafish embryos, while ztsg2 is only expressed at later stages.

MOs were used to reduce the function of the endogenous ztsg1. To visualize the vasculature, 9 ng of UroD-MO was injected into embryos. In situ hybridizations were performed for the following markers at the indicated developmental stages: MyoD (8 somite stage), Krox20 (8 somite), GATA2 (22 somite) and BMP-4 (3 somite stage). Injection of 12 ng of a ztsg1 morpholino (ztsg-MO) resulted in 50% of the injected embryos giving rise to zebrafish with phenotypes characteristic of expanded BMP signaling (Hammerschmidt et al. (1996) Develop 123:95–102; Miller-Bertoglio et al. (1999) Dev Biol 214:72–86). Embryos developed expansion of the ventral fin region that corresponded to ectopic blood islands, a tissue derived from ventral mesoderm. Injected embryos also showed an expansion of GATA2 at the 22 somite stage of development (48%, n=21), loss of paraxial mesoderm (visualized with the marker MyoD) at the 8 somite stage (38%, n=33), and a mild reduction of anterior ectodermal tissues (detected by staining for Krox-20) at the 8 somite stage (49%, n=39). Caudal expression of BMP4 also was expanded in these embryos at the 3 somite stage (48%, n=25), while the anterior ectodermal marker otx-2 was reduced. Treated embryos also exhibited an expansion in apoptotic cells ventral to the yolk extension similar to dino and mercedes mutants (Hammerschmidt et al. (1996) Develop 123:95–102; Fisher et al. (1997) Develop 124:1301–11). Overall, this phenotype is very similar to that of ogon/mercedes mutants (Hammerschmidt et al. (1996) Develop 123:95–102; Miller-Bertoglio et al. (1999) Dev Biol 214:72–86) and moderate chordin loss-of-function mutants, and represents a modest ventralized phenotype (Nasevicius et al. (2000) Nat Gen 26:216–220; Hammerschmidt et al. (1996) Develop 123:95–102).

Injection of ztsg1 mRNA resulted in phenotypes diagnostic of reduced BMP signaling (Mullins et al. (1996) Develop 123:81–93; Kishimoto et al. (1997) Develop 124:4457–66; Dick et al (2000) Develop 127:343–54). Injection of 75 pg of ztsg1 mRNA resulted in 56% of the surviving animals (164 injected, 108 alive) exhibiting reduced axial length with loss of ventral fin. This is a phenocopy of the C3-C4 class of dorsalized mutant embryos observed with the snailhouse (BMP-7 homologue) and piggytail mutations (Mullins et al. (1996) Develop 123:81–93; Dick et al. (2000) Develop 127:343–54). Molecular analysis revealed a similar expansion of MyoD (50%, n=8) and Krox20 (70%, n=10) at the 8 somite stage. Furthermore, the dorsalizing effect of ztsg1 mRNA partially reversed the ventralizing effect of the ztsg1-MO (9 ng tsg1-MO caused 47±2% ventralized embryos (n=376); 9 ng ztsg1-MO plus 30 pg ztsg1 mRNA resulted in 19±8% ventralized embryos (n=270)) indicating that loss of ztsg1 was responsible for the phenotype. Therefore, loss of ztsg1 led to embryos with a ventralized phenotype, while ectopic expression of ztsg1 led to a dorsalized embryonic phenotype.

Example 27

Figure 10:
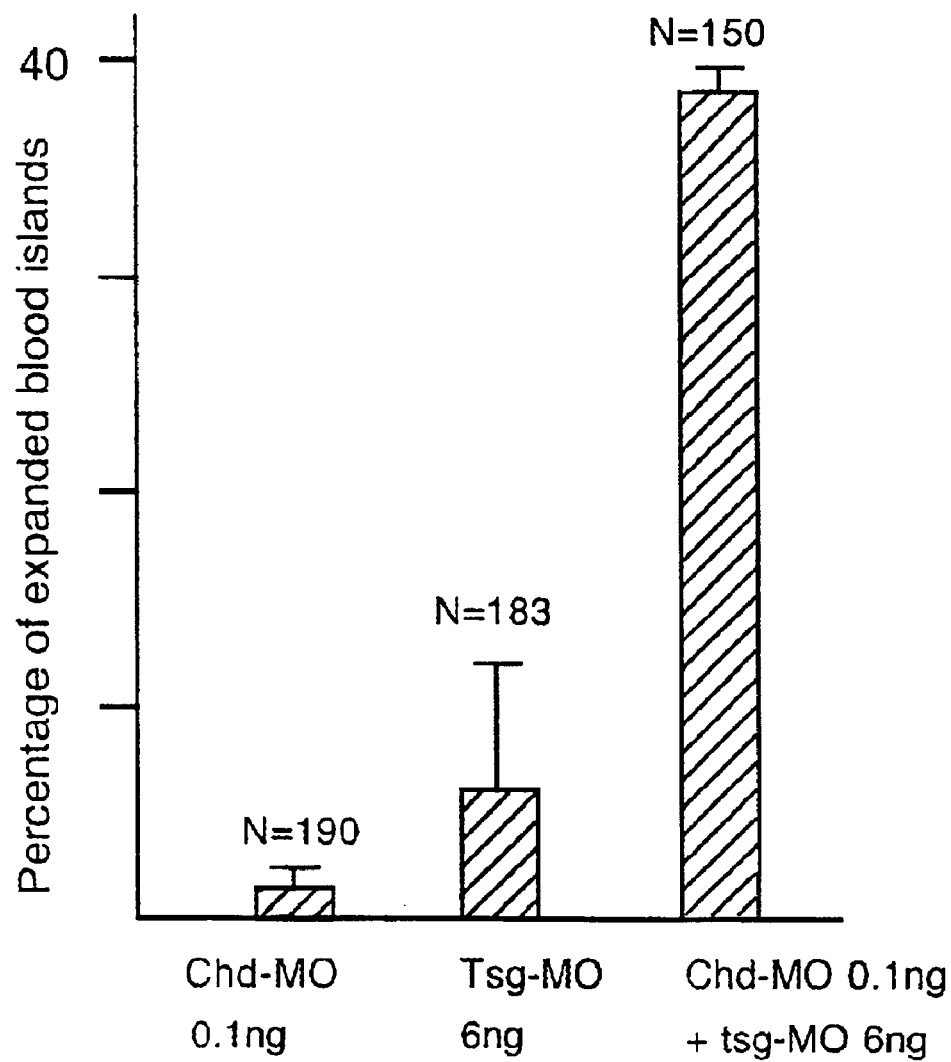
FIG. 10 is a bar graph demonstrating the synergistic effects of ztsg1- and chordin-MO on blood island expansion.

Enhancement of the ztsg1 Loss-of-function Phenotype by Sub-inhibitory Loss of the Chordin Gene Drosophila data suggest that one role of Tsg is to potentiate the inhibition of BMP signaling in conjunction with Sog/Chordin. To determine if the same is true for vertebrates, sub-inhibitory levels of chordin-MO and ztsg1-MO were injected into wild type embryos and the effect on ectopic blood island development was scored. Embryos were injected with either a low dose of ztsg1-MO, chordin-MO, or both ztsg1-MO and chordin-MO, and the resulting embryos were examined for blood island expansion. Results, depicted in FIG. 10, demonstrate that ztsg1-MO and chordin-MO synergistically enhanced blood island expansion. Co-injection of sub-inhibitory levels of MOs directed against both Tsg and Chordin synergistically enhances the penetrance of the ventralized phenotype. Therefore, both gene products cooperatively inhibited BMP signaling. The finding that Tsg and Chordin cooperate to inhibit BMP-2 signalling was confirmed by results of biochemical experiments performed in Drosophila as well as in Xenopus (See Ross et al. (2001) Nature 410:479–83.)

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for producing a zebrafish embryo comprising a polynucleotide analogue, wherein said polynucleotide analogue is selected from the group consisting of a morpholino-modified polynucleotide, a 3'-5' phosphoroamidate, a peptide nucleic acid, and a polynucleotide comprising a ribose moiety having a 2' O-methyl group, wherein said polynucleotide analogue is present in an amount effective to reduce expression from a selected nucleic acid that is expressed during zebrafish embryonic development, said method comprising contacting said embryo, or an egg giving rise to said embryo, with said polynucleotide analogue, wherein said reduction in expression of said selected nucleic acid persists at least to larval or post-hatching stages of development.

2. The method of claim 1, wherein said polynucleotide analogue is a morpholino-modified polynucleotide.

3. The method of claim 1, wherein said polynucleotide analogue is a 3'-5' phosphoroamidate.

4. The method of claim 1, wherein said polynucleotide analogue is a peptide nucleic acid.

5. The method of claim 1, wherein said polynucleotide analogue comprises a ribose moiety having a 2' O-methyl group.

6. The method of claim 1, wherein said polynucleotide analogue is complementary to a region of said selected nucleic acid that comprises a 5' untranslated region.

7. The method of claim 1, wherein said polynucleotide analogue is complementary to a region of said selected nucleic acid that comprises part of or an entire AUG start codon.

8. The method of claim 1, wherein said polynucleotide analogue is complementary to a region of said selected nucleic acid that comprises the coding region.

* * * * *

UNITED STATES PATENT AND TRADEMARK OFFICE
CERTIFICATE OF CORRECTION

PATENT NO. : 6,867,349 B2
DATED : March 15, 2005
INVENTOR(S) : Stephen C. Ekker et al.

It is certified that error appears in the above-identified patent and that said Letters Patent is hereby corrected as shown below:

Title page,
Item [56], References Cited, OTHER PUBLICATIONS,
"Krauss et al." reference, delete "genes" and insert -- gene --;
"Zhang et al." reference, delete "EGP" and insert -- EGF --.

Signed and Sealed this

Twentieth Day of December, 2005

JON W. DUDAS
*Director of the United States Patent and Trademark Office*

SEQUENCE LISTING

<160> NUMBER OF SEQ ID NOS: 25

<210> SEQ ID NO 1
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 1
atccacagca gccctccat catcc                                          25

<210> SEQ ID NO 2
<211> LENGTH: 14
<212> TYPE: DNA
<213> ORGANISM: Artificial Sequence
<220> FEATURE:
<223> OTHER INFORMATION: Synthetically generated oligonucleotide

<400> SEQUENCE: 2
agcagcccct ccat                                                     14

<210> SEQ ID NO 3
<211> LENGTH: 17
<212> TYPE: DNA
<213> ORGANISM: Artificial Sequence
<220> FEATURE:
<223> OTHER INFORMATION: Synthetically generated oligonucleotide
<221> NAME/KEY: misc_feature
<222> LOCATION: 10, 12, 14, 16
<223> OTHER INFORMATION: n = pseudoisocytosine
<221> NAME/KEY: misc_feature
<222> LOCATION: 9
<223> OTHER INFORMATION: n = A,T,C or G

<400> SEQUENCE: 3
tctctctcnn tntntnt                                                  17

<210> SEQ ID NO 4
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 4
cctcttacct cagttacaat ttata                                         25

<210> SEQ ID NO 5
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 5
atccacagca gccctccat catcc                                          25

<210> SEQ ID NO 6
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 6
tcttctcctt tactcatttt ctacc                                              25

<210> SEQ ID NO 7
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 7
tctactcgtt tactcattat cttcc                                              25

<210> SEQ ID NO 8
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 8
gccaataaac tccaaaacaa ctcga                                              25

<210> SEQ ID NO 9
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 9
gacttgaggc aggcatattt ccgat                                              25

<210> SEQ ID NO 10
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 10
cagcactctc gtcaaaagcc gcatt                                              25

<210> SEQ ID NO 11
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 11
tgtctagcag ggtttctcgt tgtcg                                              25

<210> SEQ ID NO 12
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 12
ttccatgacg tttgaattat ctctt                                              25

<210> SEQ ID NO 13
<211> LENGTH: 25
<212> TYPE: DNA

```
<213> ORGANISM: Artificial Sequence
<220> FEATURE:
<223> OTHER INFORMATION: Synthetically generated oligonucleotide

<400> SEQUENCE: 13
catgttcaac tatgtgttag cttca                                              25

<210> SEQ ID NO 14
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 14
tataagtcca tctatctcat gtgtg                                              25

<210> SEQ ID NO 15
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 15
gaatgaaact gtccttatcc atca                                               24

<210> SEQ ID NO 16
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 16
gtatcaaata aacaaccaag ttcat                                              25

<210> SEQ ID NO 17
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 17
gtaacaatta aacaaccatg ttgat                                              25

<210> SEQ ID NO 18
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 18
taagaaagcg aagctgctgg gtatg                                              25

<210> SEQ ID NO 19
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 19
ctgatgatga tgatgaagac cccat                                              25
```

```
<210> SEQ ID NO 20
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 20
cacacacact tccactcgcc tgcat                                   25

<210> SEQ ID NO 21
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 21
cctgcattgt ctcgaaaagt tccgc                                   25

<210> SEQ ID NO 22
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 22
caattttcag tggagcccga caata                                   25

<210> SEQ ID NO 23
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 23
taatagttcc gtccattttc cgcaa                                   25

<210> SEQ ID NO 24
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 24
tccgtccatt ttccgcaatt ttcag                                   25

<210> SEQ ID NO 25
<211> LENGTH: 25
<212> TYPE: RNA
<213> ORGANISM: Artificial Sequence
<220> FEATURE:
<223> OTHER INFORMATION: Synthetically generated oligonucleotide

<400> SEQUENCE: 25
auccacagca gccccuccau caucc                                   25
```